United States Patent
Yamada et al.

(10) Patent No.: US 9,872,658 B2
(45) Date of Patent: Jan. 23, 2018

(54) MEDICAL IMAGING DIAGNOSIS APPARATUS, NUCLEAR MEDICINE DIAGNOSIS APPARATUS, X-RAY CT APPARATUS, AND BED APPARATUS

(71) Applicant: Toshiba Medical Systems Corporation, Otawara-shi (JP)

(72) Inventors: Yasunobu Yamada, Nasushiobara (JP); Katsuhito Morino, Utsunomiya (JP); Tomoyasu Komori, Otawara (JP); Masakazu Matsuura, Nasushiobara (JP); Hisashi Yasuda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 212 days.

(21) Appl. No.: 14/749,125

(22) Filed: Jun. 24, 2015

(65) Prior Publication Data

US 2015/0289829 A1 Oct. 15, 2015

Related U.S. Application Data

(63) Continuation of application No. PCT/JP2014/050163, filed on Jan. 8, 2014.

(30) Foreign Application Priority Data

Jan. 8, 2013 (JP) .................................. 2013-001259
Jan. 8, 2014 (JP) .................................. 2014-001586

(51) Int. Cl.
*A61B 6/00* (2006.01)
*A61B 6/03* (2006.01)
*A61B 6/04* (2006.01)

(52) U.S. Cl.
CPC ............ *A61B 6/4417* (2013.01); *A61B 6/032* (2013.01); *A61B 6/035* (2013.01); *A61B 6/037* (2013.01);
(Continued)

(58) Field of Classification Search
CPC ......... A61B 6/032; A61B 6/035; A61B 6/037; A61B 6/4417; A61B 6/56; A61B 6/563; A61B 6/566; A61B 6/583
(Continued)

(56) References Cited

U.S. PATENT DOCUMENTS 5,241,181 A * 8/1993 Mertens ................ G01T 1/2985
250/363.03
6,205,347 B1 * 3/2001 Morgan ................... A61B 6/04
600/407

(Continued)

FOREIGN PATENT DOCUMENTS

JP 09-5441 A 1/1997
JP 2001-314397 A 11/2001
(Continued)

OTHER PUBLICATIONS

International Search Report dated Mar. 4, 2014 for PCT/JP2014/050163 filed Jan. 8, 2014 with English Translation.
(Continued)

*Primary Examiner* — Allen C. Ho
(74) *Attorney, Agent, or Firm* — Oblon, McClelland, Maier & Neustadt, L.L.P.

(57) ABSTRACT

According to one embodiment, a medical imaging diagnosis apparatus includes a top-plate, a bed, a first gantry, a second gantry and a moving assembly. The top-plate places a subject thereon. The bed supports the top-plate. The first gantry includes an X-ray generator and an X-ray detector which revolve around the top-plate. The second gantry
(Continued)

includes a gamma ray detector which detects gamma rays emitted from the subject. The moving assembly moves, based on a first position indicative of a center position of an effective view field in the first gantry and a second position indicative of a center position of an effective view field in the second gantry, the top-plate relative to the second position.

11 Claims, 12 Drawing Sheets

(52) U.S. Cl.
CPC .............. *A61B 6/0407* (2013.01); *A61B 6/56* (2013.01); *A61B 6/563* (2013.01); *A61B 6/566* (2013.01); *A61B 6/583* (2013.01); *A61B 6/5205* (2013.01); *A61B 6/547* (2013.01)

(58) Field of Classification Search
USPC .................. 378/20, 207; 250/363.02–363.09
See application file for complete search history.

(56) References Cited

U.S. PATENT DOCUMENTS

| | | | | |
|---|---|---|---|---|
| 6,298,112 B1* | 10/2001 | Acharya | ................. | A61B 6/032 378/15 |
| 6,449,331 B1* | 9/2002 | Nutt | ....................... | A61B 6/032 250/363.04 |
| 6,490,476 B1* | 12/2002 | Townsend | ............. | A61B 6/032 250/363.03 |
| 6,539,074 B1* | 3/2003 | Yavuz | .................... | A61B 6/032 378/4 |
| 6,754,519 B1* | 6/2004 | Hefetz | ................... | A61B 6/032 600/407 |
| 6,754,520 B2* | 6/2004 | DeSilets | ............... | A61B 6/032 128/906 |
| 6,920,196 B2* | 7/2005 | Ueno | .................... | A61B 6/032 250/363.03 |
| 6,928,142 B2* | 8/2005 | Shao | ...................... | A61B 6/037 250/363.04 |
| 6,961,606 B2* | 11/2005 | DeSilets | ............... | A61B 6/032 128/906 |
| 6,965,661 B2* | 11/2005 | Kojima | .................. | A61B 6/037 378/10 |
| 7,103,233 B2* | 9/2006 | Stearns | ..................... | G06T 7/30 378/4 |
| 7,149,565 B2* | 12/2006 | Kojima | .................. | A61B 6/032 250/363.03 |
| 7,154,096 B2* | 12/2006 | Amano | .................. | A61B 6/032 250/363.03 |
| 7,162,004 B2* | 1/2007 | Inoue | .................... | A61B 6/032 250/363.04 |
| 7,254,438 B2* | 8/2007 | DeSilets | ................. | A61B 6/00 250/363.02 |
| 7,291,840 B2* | 11/2007 | Fritzler | ................. | G01T 1/2985 250/363.03 |
| 7,292,673 B2* | 11/2007 | Kröner | .................. | A61B 6/032 250/363.03 |
| 7,297,958 B2* | 11/2007 | Kojima | ................ | A61B 6/4241 250/363.03 |
| 7,348,564 B2* | 3/2008 | Wollenweber | ......... | A61B 6/032 250/363.02 |
| 7,357,575 B2* | 4/2008 | Huber | ................... | A61B 6/032 378/20 |
| 7,374,337 B2* | 5/2008 | Yunker | .................... | A61B 6/00 250/363.02 |
| 7,382,851 B2* | 6/2008 | Inoue | ..................... | A61B 6/032 250/363.04 |
| 7,412,027 B2* | 8/2008 | Yakubovsky | ............ | A61B 6/04 378/195 |
| 7,412,280 B2* | 8/2008 | Hertel | .................... | A61B 6/032 600/407 |
| 7,447,345 B2* | 11/2008 | Shanmugam | .......... | A61B 6/032 250/363.03 |
| 7,507,968 B2* | 3/2009 | Wollenweber | ......... | A61B 6/032 250/363.07 |
| 7,558,439 B2* | 7/2009 | Weese | ....................... | G06T 5/50 382/294 |
| 7,564,945 B2* | 7/2009 | Kim | ...................... | A61B 6/4447 378/17 |
| 7,639,782 B2* | 12/2009 | Zelnik | ...................... | A61B 6/04 378/195 |
| 7,652,256 B2* | 1/2010 | Lusser | .................... | G01T 1/249 250/363.02 |
| 7,683,338 B2* | 3/2010 | Ueno | ...................... | A61B 6/032 250/370.09 |
| 7,697,738 B2* | 4/2010 | Da Silva | .................. | A61B 6/12 382/128 |
| 7,941,203 B2* | 5/2011 | Zheng | .................... | A61B 6/032 5/630 |
| 7,991,115 B2* | 8/2011 | Matsuzawa | ............ | A61B 6/032 250/394 |
| 8,077,943 B2* | 12/2011 | Williams | ............... | A61B 6/037 378/205 |
| 8,498,464 B2* | 7/2013 | Xu | ......................... | A61B 6/032 378/20 |
| 8,553,961 B2* | 10/2013 | Zhu | ........................... | G06T 7/38 382/131 |
| 8,989,845 B2* | 3/2015 | Brinks | .................... | A61B 6/032 378/4 |
| 9,129,370 B2* | 9/2015 | Motomura | ............ | G06T 7/0028 |
| 9,240,045 B2* | 1/2016 | Noshi | ................... | A61B 6/0407 |
| 9,305,377 B2* | 4/2016 | Olivier | .................. | G06T 11/005 |
| 9,317,942 B2* | 4/2016 | Olivier | .................. | G06T 11/008 |
| 9,336,614 B1* | 5/2016 | Wollenweber | ......... | G06T 11/008 |
| 2003/0212320 A1* | 11/2003 | Wilk | ....................... | A61B 6/032 600/407 |
| 2008/0212859 A1 | 9/2008 | Da Silva et al. | | |
| 2009/0087061 A1 | 4/2009 | Xu et al. | | |
| 2010/0158336 A1* | 6/2010 | Motomura | ............. | A61B 6/032 382/131 |

FOREIGN PATENT DOCUMENTS

| | | | |
|---|---|---|---|
| JP | 2007-503238 A | 2/2007 | |
| JP | 2007-222599 A | 9/2007 | |
| JP | 2008-183142 A | 8/2008 | |
| JP | 2010-004959 A | 1/2010 | |
| JP | 2010-167261 A | 8/2010 | |
| JP | 2011-092554 A | 5/2011 | |

OTHER PUBLICATIONS

International Written Opinion dated Mar. 4, 2014 for PCT/JP2014/050163 filed Jan. 8, 2014.
Combined Chinese Office Action and Search Report dated Mar. 14, 2017 in Chinese Patent Application No. 201480004220.X (with English translation of categories of cited documents).

* cited by examiner

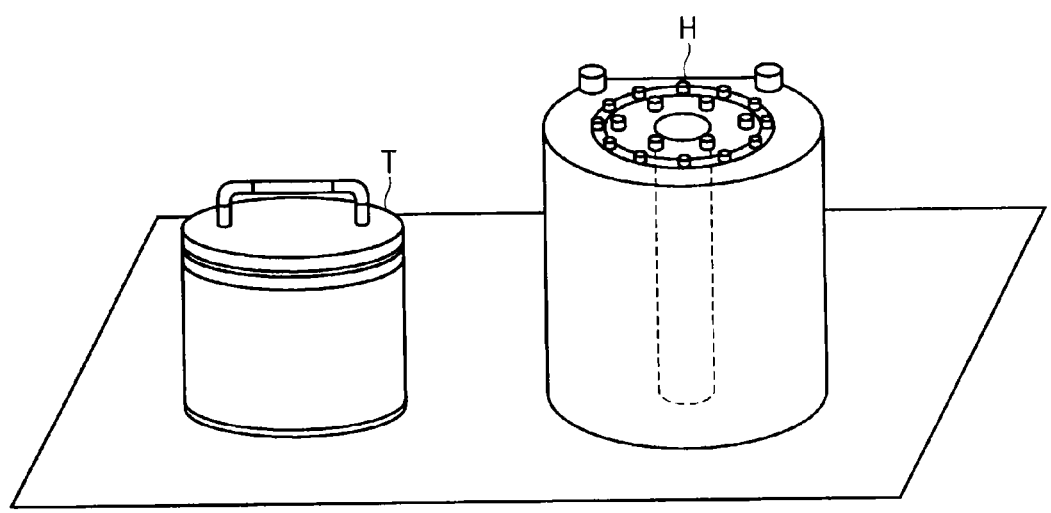
F I G. 5

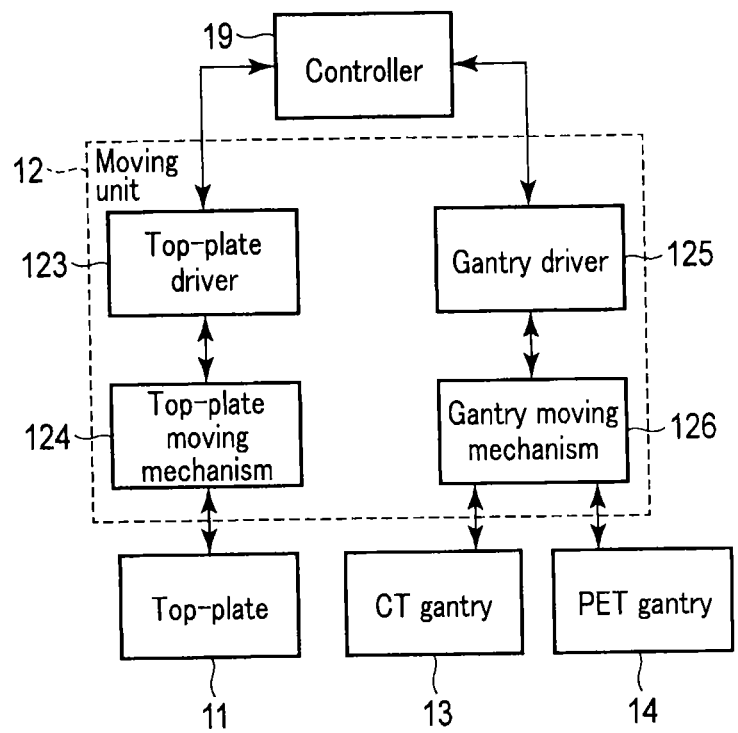
F I G. 8
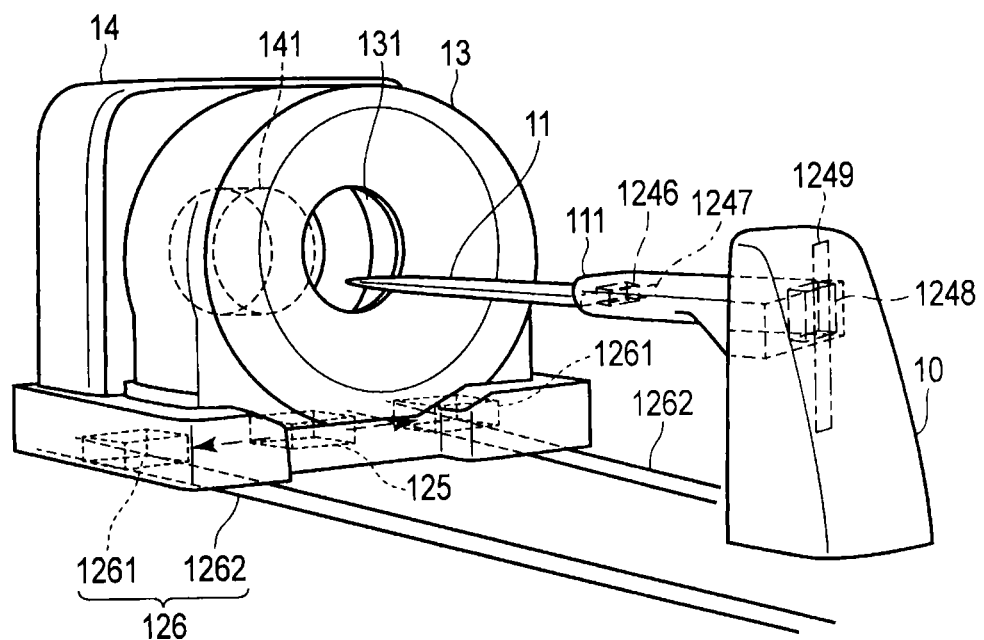
F I G. 9

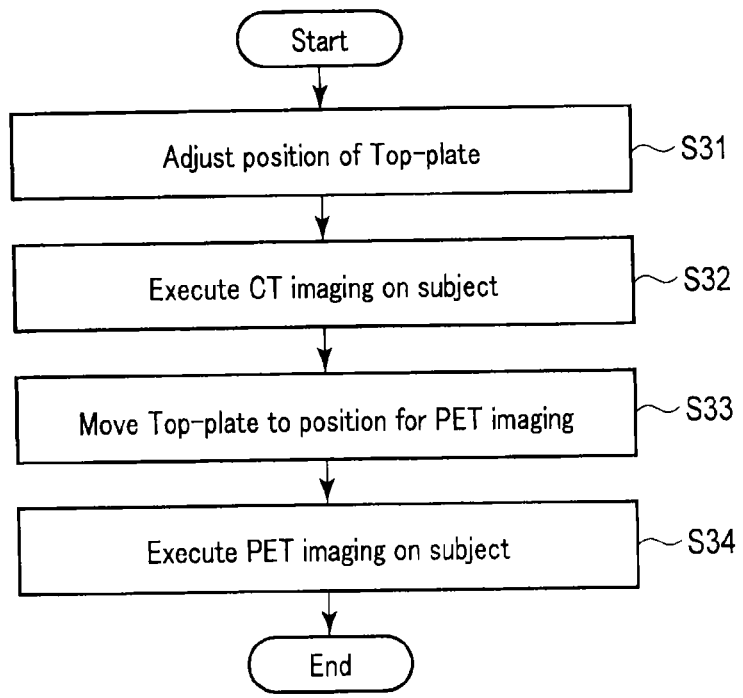
F I G. 11
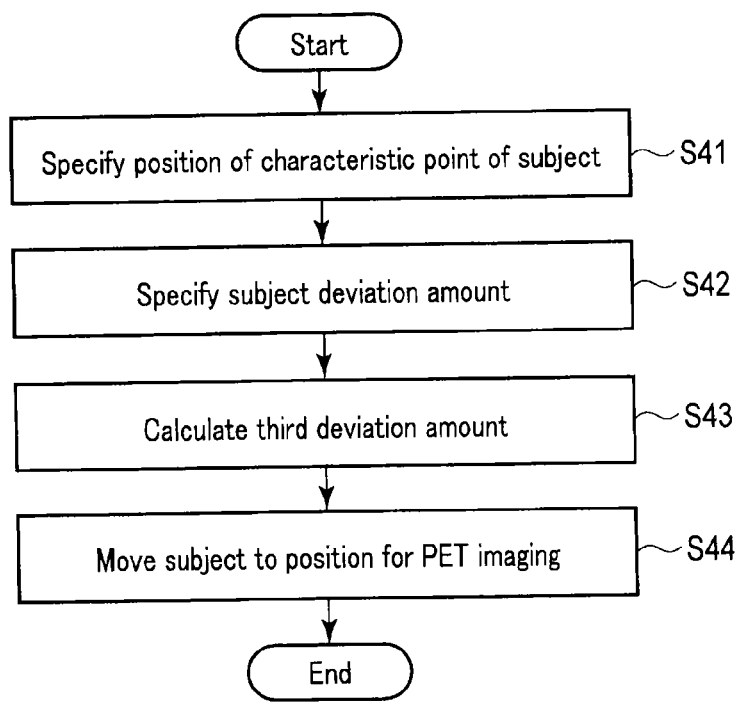
F I G. 12

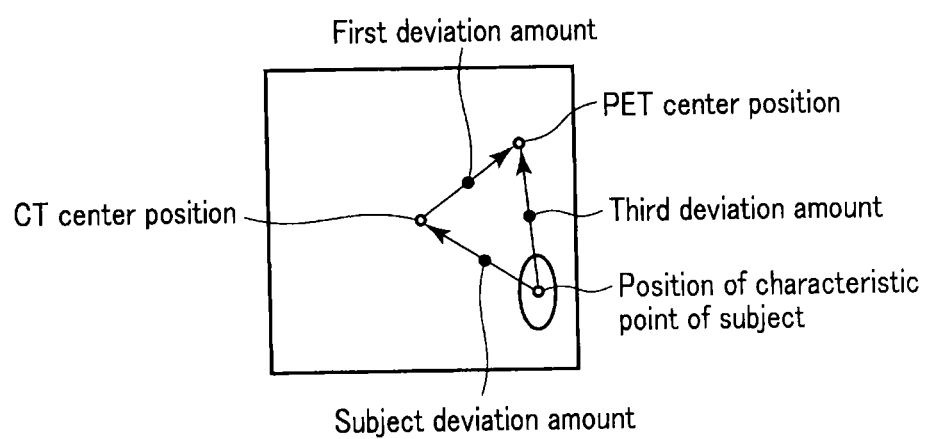
F I G. 13

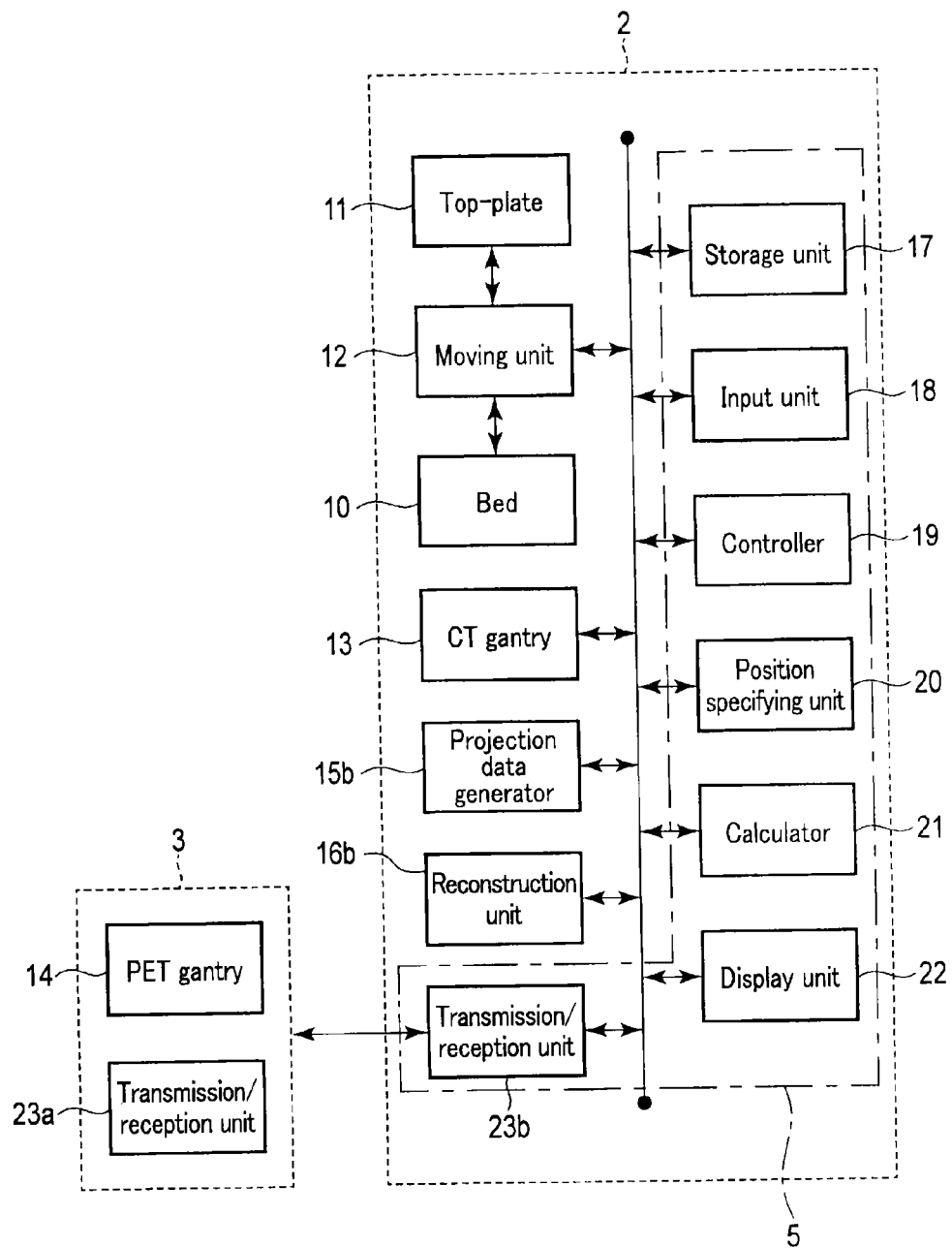
F I G. 14

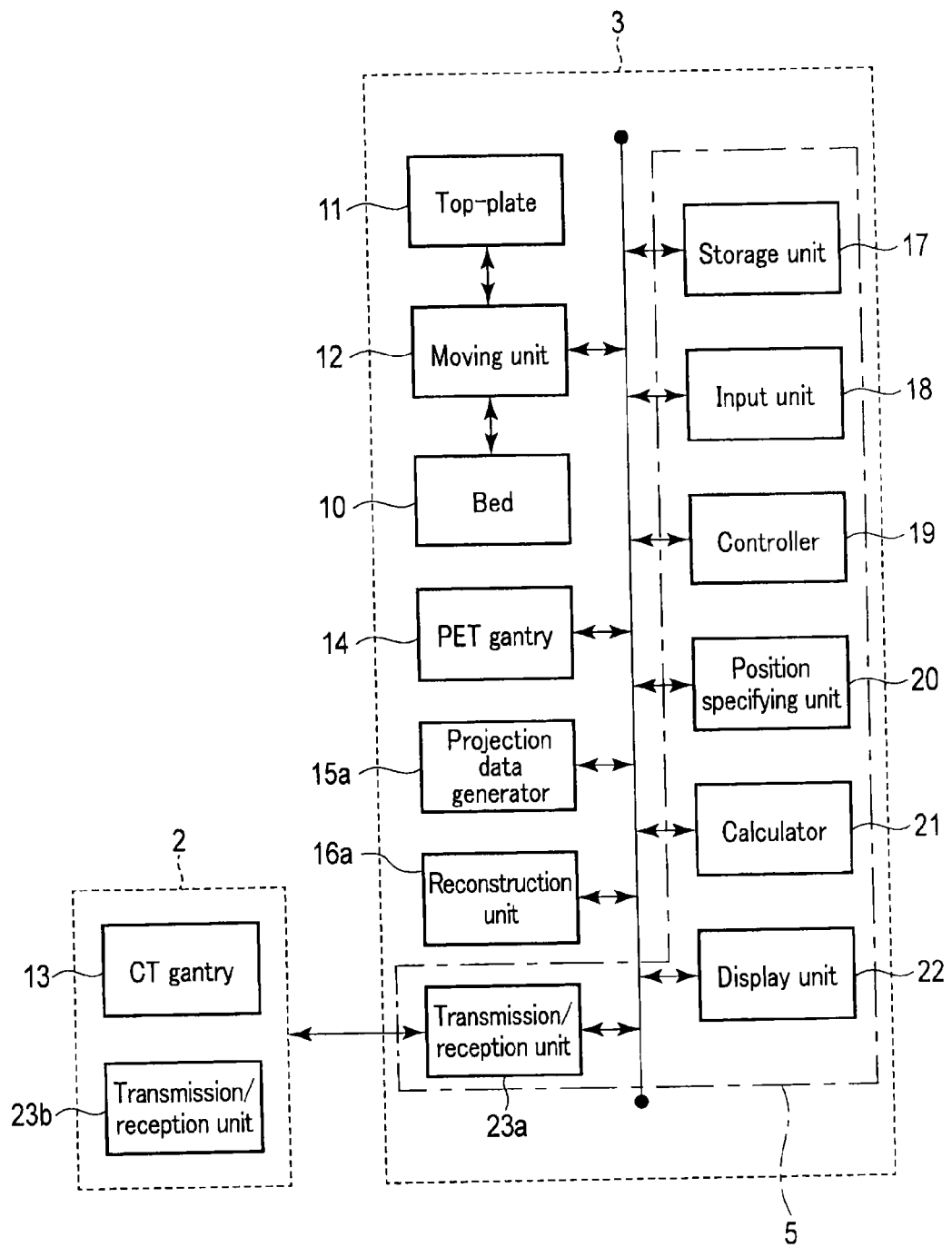
F I G. 15 though the calibration work cannot exactly be carried out. In addition, in the case of actually imaging a subject by the nuclear medicine diagnosis apparatus, the setting of the subject is adjusted by, for example, a top-plate operation by the operator, with a projector being used as a guide. Thus, there is a case in which the subject is not set at the center position

MEDICAL IMAGING DIAGNOSIS APPARATUS, NUCLEAR MEDICINE DIAGNOSIS APPARATUS, X-RAY CT APPARATUS, AND BED APPARATUS

CROSS-REFERENCE TO RELATED APPLICATIONS

This application is a Continuation Application of PCT Application No. PCT/JP2014/050163, filed Jan. 8, 2014 and based upon and claiming the benefit of priority from prior Japanese Patent Applications No. 2013-001259, filed Jan. 8, 2013 and No. 2014-001586, filed Jan. 8, 2014, the entire contents of all of which are incorporated herein by reference.

FIELD

Embodiments of the present invention relate to a medical imaging diagnosis apparatus, an X-ray CT apparatus, a nuclear medicine diagnosis apparatus, and a bed apparatus.

BACKGROUND

In recent years, with the development of medical technology, medical imaging diagnosis apparatuses, in each of which an X-ray CT apparatus and a nuclear medicine diagnosis apparatus are combined, have been quickly gaining in popularity, as exemplified by a PET-CT apparatus in which an X-ray CT (Computed Tomography) apparatus and a PET (Positron Emission Tomography) are combined, and a SPECT-CT apparatus in which an X-ray CT apparatus and a SPECT (Single-Photon Emission Computed Tomography) apparatus are combined. In such a medical imaging diagnosis apparatus, the CT apparatus generates a morphological image which reflects an anatomical position of a photographed region. On the other hand, the nuclear medicine diagnosis apparatus generates a functional image which reflects intravital biochemical and physiological functions and metabolic information. The medical imaging diagnosis apparatus, in which the X-ray CT apparatus and nuclear medicine diagnosis apparatus are combined, generates a fusion image in which the morphological image and functional image are fused. The morphological image and functional image have a complementary relationship. Thus, the fusion image serves as an image for diagnosis of a patient with higher precision.

In order to generate a high-precision fusion image, measurements by the X-ray CT apparatus and nuclear medicine diagnosis apparatus need to be performed with high precision. For example, in the nuclear medicine diagnosis apparatus, a calibration work of a gamma ray detector needs to be exactly performed. In order to exactly perform the calibration work, it is necessary to exactly set a phantom, which is used for calibration, at the center position of the effective view field of the nuclear medicine diagnosis apparatus.

However, conventionally, setting of a phantom on a top-plate is manually performed by an operator, with a projector being used as a guide. Consequently, there is a case in which the phantom is not set at the center position of the actual effective view field, and there is a case in which the calibration work cannot exactly be carried out. In addition, in the case of actually imaging a subject by the nuclear medicine diagnosis apparatus, the setting of the subject is adjusted by, for example, a top-plate operation by the operator, with a projector being used as a guide. Thus, there is a case in which the subject is not set at the center position of the actual effective view field, and there is a possibility that measurement cannot exactly be performed.

BRIEF DESCRIPTION OF DRAWINGS

FIG. 5 relates to the first embodiment, and is a perspective view illustrating an example of a phantom used in, for example, calibration of a gamma ray detector;

FIG. 8 is a configuration diagram illustrating an example of the configuration of a moving unit in a medical imaging diagnosis apparatus according to a second embodiment;

FIG. 9 relates to the second embodiment, and is a perspective view illustrating an example of the positional relationship between first and second gantries, a bed and a top-plate;

FIG. 11 is a flowchart illustrating an example of an imaging procedure of a subject with use of a medical imaging diagnosis apparatus 1 according to a third embodiment;

FIG. 12 is a flowchart illustrating an example of the procedure of step S33;

FIG. 13 is an explanatory view for explaining a third deviation amount which is calculated by a calculator 21;

FIG. 14 is a configuration diagram illustrating an example of the configuration of an X-ray CT apparatus according to a fourth embodiment;

FIG. 15 is a configuration diagram illustrating an example of the configuration of a nuclear medicine diagnosis apparatus according to a fifth embodiment.

DETAILED DESCRIPTION

Figure 1:
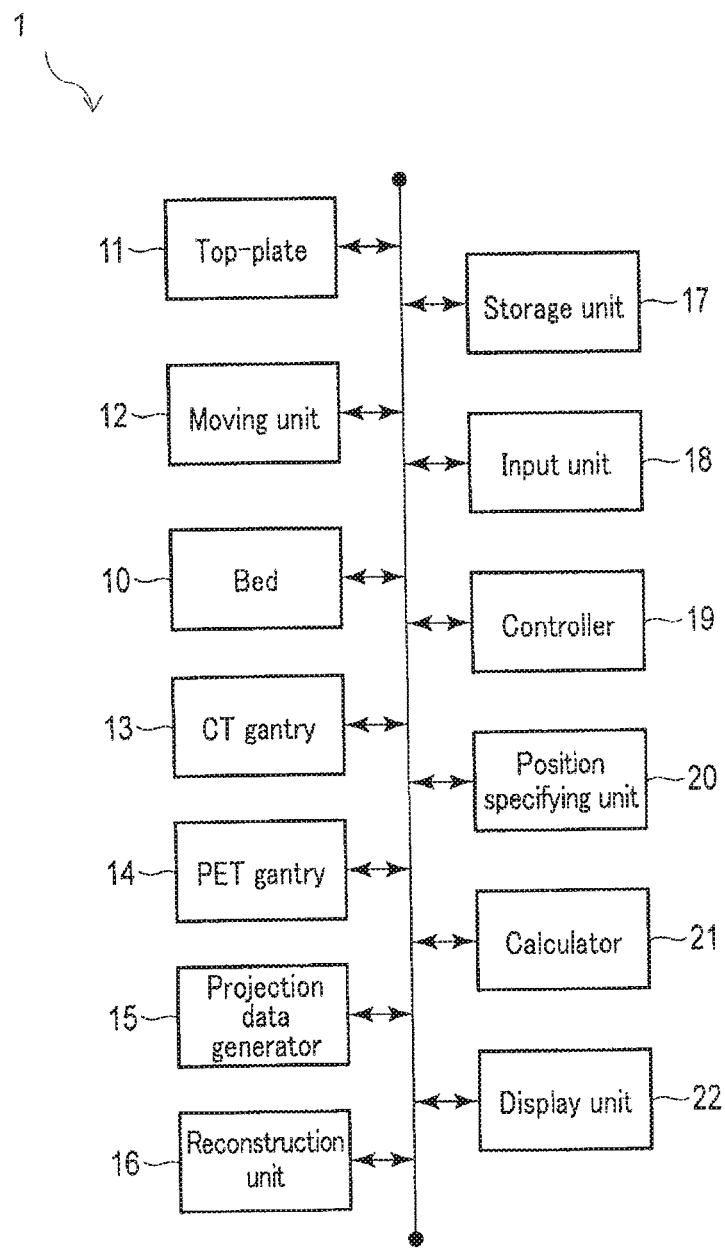
FIG. 1 is a configuration diagram illustrating an example of the configuration of a medical imaging diagnosis apparatus according to a first embodiment.

According to one embodiment, a medical imaging diagnosis apparatus includes a top-plate, a bed, a first gantry, a second gantry and a moving assembly. The top-plate places a subject thereon. The bed supports the top-plate. The first gantry includes an X-ray generator and an X-ray detector which revolve around the top-plate. The second gantry includes a gamma ray detector which detects gamma rays emitted from the subject. The moving assembly moves, based on a first position indicative of a center position of an effective view field in the first gantry and a second position indicative of a center position of an effective view field in the second gantry, the top-plate relative to the second position.

Hereinafter, referring to the accompanying drawings, medical imaging diagnosis apparatuses according to first and second embodiments of the present invention will be described. In the description below, structural elements having substantially the same functions and structures are denoted by like reference numerals, and an overlapping description is given only where necessary.

In the first and second embodiments, for the purpose of simple description, as an example of the medical imaging diagnosis apparatus, a PET-CT apparatus is described in which a positron emission computed tomography (hereinafter referred to as "PET") apparatus, which is a nuclear medicine diagnosis apparatus, and an X-ray computed tomography (hereinafter referred to as "CT") apparatus, are combined. Incidentally, the first embodiment is also applicable to a SPECT-CT apparatus in which a single-photon emission computed tomography (hereinafter referred to as "SPECT") apparatus, which is a nuclear medicine diagnosis apparatus, and a CT apparatus are combined. Furthermore, the application to a medical imaging diagnosis apparatus 1, in which some other nuclear medicine diagnosis apparatus and a CT apparatus are combined, is also possible.

First Embodiment

FIG. 1 is a configuration diagram illustrating an example of the configuration of the medical imaging diagnosis apparatus 1 according to the first embodiment. As illustrated in FIG. 1, the medical imaging diagnosis apparatus 1 includes a bed 10, a top-plate 11, a moving unit 12 (moving assembly), a first gantry 13 (hereinafter referred to as "CT gantry 13"), a second gantry 14 (hereinafter referred to as "PET gantry 14"), a projection data generator 15, a reconstruction unit 16, a storage unit 17, an input unit 18, a controller 19, a position specifying unit 20, a calculator 21, and a display unit 22.

The bed 10 supports the top-plate 11 on which a phantom is placed, such that the top-plate 11 is movable in three orthogonal axes. It is assumed that the three orthogonal axes are defined by, for example, a minor axis of the top-plate 11, a major axis of the top-plate 11, and an orthogonal axis which is perpendicular to the minor axis and major axis. Hereinafter, a direction along the major axis of the top-plate 11 is referred to as a major-axis direction. In addition, a direction along the minor axis of the top-plate 11 is referred to as a minor-axis direction. Besides, a direction along the orthogonal axis of the top-plate 11 is referred to as an orthogonal-axis direction.

The moving unit 12 moves the top-plate 11 relative to a center position (hereinafter referred to as "PET center position") of the effective view field of the PET gantry (to be described later), in accordance with control by the controller 19 (to be described later). A detailed description of the function of the moving unit 12 will be given later.

The CT gantry 13 includes an X-ray generator and an X-ray detector. The X-ray generator includes a high voltage generator and an X-ray tube. The X-ray tube and X-ray detector are disposed to be opposed to each other, with the top-plate 11 being interposed. The high voltage generator generates a tube voltage, which is applied to the X-ray tube, and a tube current, which is supplied to the X-ray tube. The X-ray tube receives application of a tube voltage and supply of a tube current from the high voltage generator, and radiates X-rays from a focal point of X-rays. The X-ray detector detects X-rays which have been generated from the X-ray tube and have passed through a subject. The X-ray detector generates an electric signal in accordance with the detection of X-rays. The X-ray tube and X-ray detector perform X-ray generation and X-ray detection, respectively, while revolving around the top-plate 11.

The PET gantry 14 includes a gamma ray detector. The gamma ray detector is disposed, for example, in an annular shape around the top-plate 11. Incidentally, when a SPECT gantry is used in place of the PET gantry 14, the gamma ray detector is mounted on a plurality of gamma cameras or on a single gamma camera. At this time, for example, two gamma cameras are disposed to be opposed to each other, with the top-plate 11 being interposed. The gamma ray detector detects gamma rays which have been emitted from the subject. The gamma ray detector generates an electric signal corresponding to the detection of gamma rays. The positional relationship between the top-plate 11, bed 10, CT gantry 13 and PET gantry 14 will be described later.

The projection data generator 15 executes a first preprocess on the electric signal from the X-ray detector. The projection data generator 15 generates projection data (hereinafter referred to as "CT projection data"), based on the electric signal on which the first preprocess was executed. The first preprocess is, for example, logarithmic transformation, sensitivity correction, beam hardening correction, etc.

The projection data generator 15 executes a predetermined signal process on the electric signal from the gamma ray detector. The projection data generator 15 generates projection data (hereinafter referred to as "PET projection data"), based on the electric signal on which the predetermined signal process was executed. The predetermined signal process is, for example, a position calculation process, an energy calculation process, a coincidence counting process, a second preprocess, etc. The second preprocess is, for example, sensitivity correction, random correction, scattered radiation correction, etc. For these corrections, for example, use is made of each of correction values prestored in the storage unit 17 of the medical imaging diagnosis apparatus 1. Each correction value is a value generated by, e.g. PET measurement of a phantom.

The reconstruction unit 16 reconstructs, for example, a CT image relating to a predetermined cross section, based on the CT projection data. The predetermined cross section is, for example, a cross section designated by the operator. A pixel value, which is assigned to each of pixels constituting the CT image, has, for example, a CT value which corresponds to an X-ray attenuation coefficient relating to a substance on an X-ray transmission path.

The reconstruction unit 16 reconstructs, for example, a PET image relating to a cross section at substantially the same position as the reconstruction cross section of the CT image, based on the PET projection data. A pixel value, which is assigned to each of pixels constituting the PET image, corresponds to a count value which corresponds to a concentration of a radioactive isotope.

The storage unit 17 is a semiconductor storage device such as a flash SSD (Solid State Disk) that is a semiconductor storage element, an HDD (Hard Disk Drive), etc. The storage device 17 stores the CT projection data and PET projection data. Incidentally, the storage unit 17 may store data of a CT image by associating the data of the CT image with the CT projection data. In addition, the storage unit 17 may store data of a PET image by associating the data of the PET image with the PET projection data.

The storage unit 17 stores data of a first deviation amount. The first deviation amount is expressed by a distance and a direction between a center position (hereinafter referred to as "CT center position") of the effective view field of the CT gantry 13 and the PET center position.

For example, the first deviation amount is determined in advance, based on the positions (e.g. view angles) of the X-ray generator, X-ray detector and gamma ray detector in the medical imaging diagnosis apparatus 1 according to the first embodiment. Specifically, to begin with, the CT center position is determined based on the positional relationship between the X-ray tube and X-ray detector in a predetermined coordinate system (hereinafter referred to as "coordinate system"). Next, the PET center position is determined based on the position of the gamma ray detector in the predetermined coordinate system. The first deviation amount is determined based on the CT center position and PET center position determined in the predetermined coordinate system. The data of the determined first deviation amount is stored in the storage unit 17. Incidentally, the first deviation amount may be determined based on a CT image and a PET image of an identical to-be-measured object that is placed on the top-plate 11. In the meantime, the storage unit 17 may store a positional correspondency table in which the shape of a region of a phantom (hereinafter referred to as "phantom region") and the position of a characteristic point (to be described later) are associated.

The input unit 18 includes, for example, an input device such as a mouse or a keyboard. Incidentally, a trackball, a touch panel, a switch, etc. may be used as the input device. The input device 18 includes an operation console for accepting an instruction relating to a movement of the top-plate 11 from the operator. The operator can move the top-plate 11 by operating the operation console. The input unit 18 functions as an interface for inputting instruction information by the operator to the medical imaging diagnosis apparatus 1.

The controller 19 includes a CPU (Central Processing Unit) and a memory circuit. The controller 19 receives information which was input from the input unit 18, and temporarily stores the input information in the memory circuit. Then, based on the input information, the controller 19 controls the respective components of the medical imaging diagnosis apparatus 1.

Specifically, the controller 19 sets a CT imaging condition and a PET imaging condition, based on the information that was input by the operator through the input unit 18. The CT imaging condition is, for instance, a tube voltage, a tube current, etc. The PET imaging condition is, for instance, a scan time, etc. In accordance with the set conditions, the controller 19 controls the CT gantry 13 and PET gantry 14. The controller 19 controls the moving unit 12, based on an output from the calculator (to be described later). Incidentally, the controller 19 may control the moving unit 12 in accordance with a movement instruction that was input by the operator through the input unit 18. The control method of the moving unit 12 by the controller 19 will be described later.

The position specifying unit 20 specifies, in the predetermined coordinate system, a predetermined position (hereinafter referred to as "characteristic point") in the phantom region on the reconstructed CT image of the phantom. Specifically, the position specifying unit 20 specifies the phantom region, for example, by executing a threshold process on the data of each of pixel values constituting the CT image. In the predetermined coordinate system, the position specifying unit 20 specifies position coordinates of the characteristic point in the specified phantom region. The characteristic point is a point desired by the operator. The characteristic point is moved to the PET center position by the moving unit 12 (to be described later).

For example, when a phantom having a symmetric cross-sectional shape is used for, e.g. calibration of the gamma ray detector, the characteristic point is the center position of the phantom region. Incidentally, when a phantom having an asymmetric cross-sectional shape is used for, e.g. calibration of the gamma ray detector, the characteristic point is the position of the center of gravity of the phantom region.

In the meantime, the characteristic point may be a position which is input by the operator through the input unit 18. Specifically, on the CT image of the phantom displayed on the display unit 22, the position of the characteristic point, which is moved to the PET center position by the operator, is input by the mouse or the like of the input unit 18. The position specifying unit 20 specifies, in the predetermined coordinate system, the position coordinates of the characteristic point which has been input on the CT image. Incidentally, the position specifying unit 20 may determine the position of the characteristic point, based on the shape of the specified phantom region and the positional correspondency table.

The calculator 21 calculates a second deviation amount. The second deviation amount is expressed by a distance and a direction between the PET center position and the position of the characteristic point in the region of the phantom. The calculation method of the second deviation amount will be described later.

The display unit 22 displays at least one of the PET image reconstructed by the reconstruction unit 16, the CT image reconstructed by the reconstruction unit 16, and a fusion image in which the PET image and CT image are fused. Incidentally, the display unit 22 may display the second deviation amount calculated by the calculator 21. In addition, the display unit 22 may display a CT image relating to the cross section of the phantom.

Figure 2:
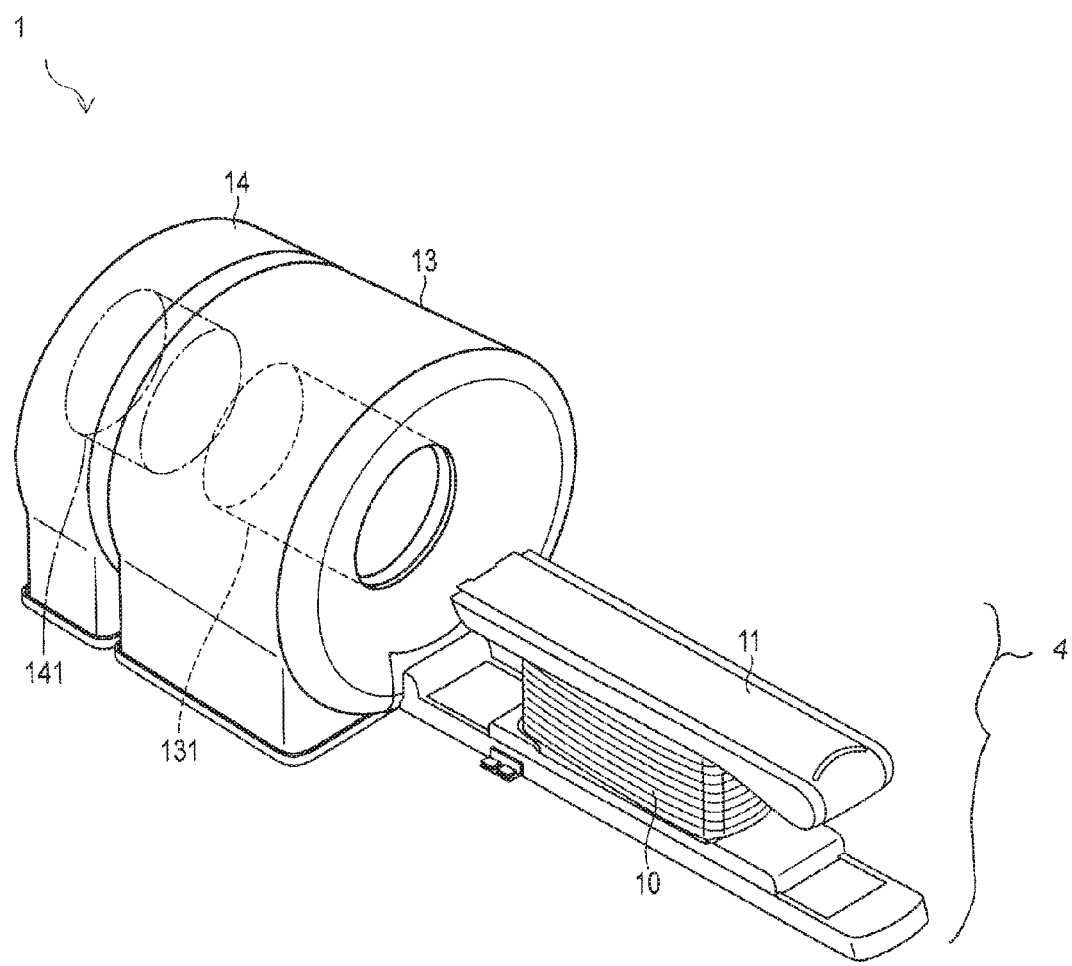
FIG. 2 relates to the first embodiment, and is a perspective view illustrating an example of the positional relationship between first and second gantries, a bed and a top-plate.

Next, referring to FIG. 2, a description is given of the positional relationship between the top-plate 11, bed 10, CT gantry 13 and PET gantry 14 in the medical imaging diagnosis apparatus 1 according to the first embodiment. FIG. 2 is a perspective view illustrating an example of the lateral positional relationship between first and second gantries, bed 10 and top-plate 11 in the medical imaging diagnosis apparatus 1 according to the first embodiment. As illustrated in FIG. 2, the CT gantry 13 includes a substantially cylindrical hollow portion 131 in which the top-plate 11 is moved. The PET gantry 14 includes a substantially cylindrical hollow portion 141 in which the top-plate 11 is moved. The CT gantry 13 and PET gantry 14 are disposed such that the center line of the hollow portion 131 and the center line of the hollow portion 141 substantially agree, for example, in the major-axis direction of the top-plate 11. Incidentally, in FIG. 2, although the CT gantry 13 and PET gantry 14 are illustrated as separate housings, the respective components in the CT gantry 13 and the respective components in the PET gantry 14 may be included in the same housing.

Figure 3:
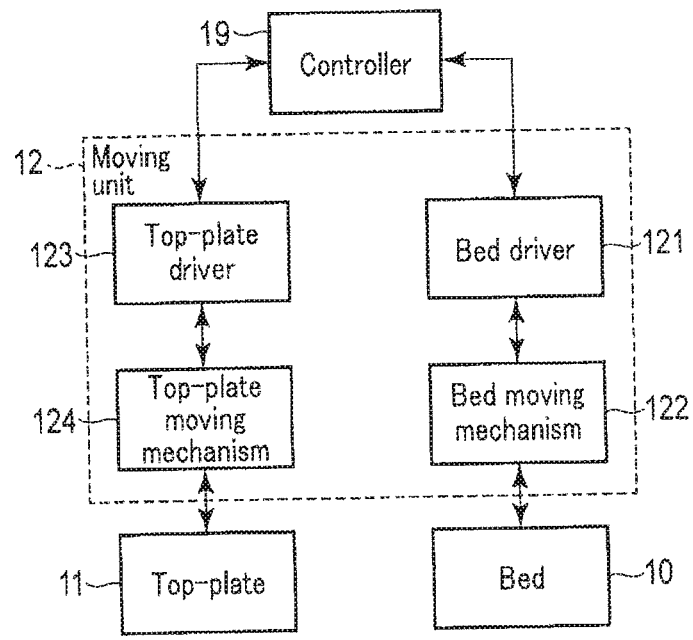
FIG. 3 is a configuration diagram illustrating an example of the configuration of a moving unit in the medical imaging diagnosis apparatus according to the first embodiment.

Next, the details of the moving unit 12 of the medical imaging diagnosis apparatus 1 according to the first embodiment are described. To begin with, the configuration of the moving unit 12 is described with reference to FIG. 3. FIG. 3 is a configuration diagram illustrating an example of the configuration of the moving unit 12 in the medical imaging diagnosis apparatus 1 according to the first embodiment. As illustrated in FIG. 3, the moving unit 12 includes a bed driver 121, a top-plate driver 123, a bed moving mechanism 122, and a top-plate moving mechanism 124.

The bed driver 121 drives the bed moving mechanism 122. The top-plate driver 123 drives the top-plate moving mechanism 124. Each of the bed driver 121 and top-plate driver 123 is, for example, a driving device such as a motor. The bed moving mechanism 122 moves the bed 10 by the driving by the bed driver 121. The top-plate moving mechanism 124 moves the top-plate 11 by the driving by the top-plate driver 123. A detailed description of the top-plate moving mechanism 124 will be given later. The bed driver 121 and top-plate driver 123 are controlled by the controller 19 according to a control method which is prestored in the storage unit 17. For example, the controller 19 preferentially controls the top-plate driver 123. The controller 19 starts control of the bed driver 121 in the case where the amount of movement, by which the top-plate 11 is moved, exceeds the range of movement of the top-plate moving mechanism 124.

Figure 4:
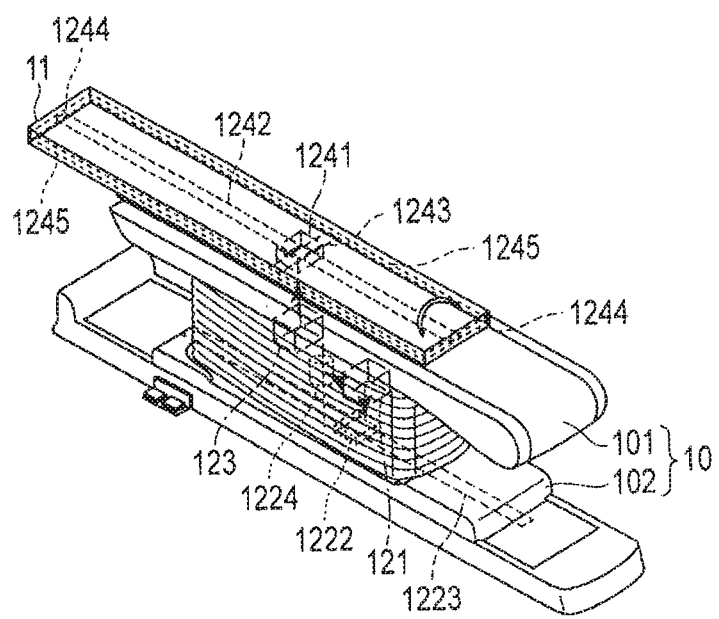
FIG. 4 relates to the first embodiment, and is an external appearance view illustrating an example of the external appearance of the top-plate and bed.

Next, referring to FIG. 4, the configuration of the moving unit 12 according to the first embodiment is described. FIG. 4 relates to the moving unit 12 of the medical imaging diagnosis apparatus 1 according to the first embodiment, and is an external appearance view illustrating an example of the external appearance of the top-plate 11 and bed 10.

As illustrated in FIG. 4, the bed moving mechanism 122 includes a first slider 1222, a first rail 1223, and a hydraulic cylinder 1224. The bed 10 includes a lower bed portion 102 and an upper bed portion 101. The top-plate 11 is supported on the upper bed portion 101. The first slider 1222 includes a bearing including a plurality of rolling elements, and is provided on the bottom surface side of the lower bed portion 102. The first rail 1223 is disposed in the major-axis direction on an installation surface on which the bed 10 is disposed. A linear motion bearing is formed by the first slider 1222 and the first rail. The hydraulic cylinder 1224 is provide between the upper bed portion 101 and lower bed portion 102.

The bed driver 121 drives the first slider 1222 in accordance with a control signal from the controller 19. By the driving of the first slider 1222, the rolling elements in the bearing roll along the first rail 1223. The bed 10 is moved in the major-axis direction by the movement of the first slider 1222. Incidentally, wheels or the like may be used in place of the slider.

The bed driver 121 drives the hydraulic cylinder 1224 in accordance with a control signal from the controller 19. By the driving of the bed driver 121, the hydraulic cylinder 1224 is extended/retracted in the orthogonal-axis direction. The bed 10 is extended/retracted in the orthogonal-axis direction in accordance with the extension/retraction operation of the hydraulic cylinder 1224. Incidentally, a pneumatic cylinder, an actuator, or a linear motion bearing along the orthogonal-axis direction may be used in place of the hydraulic cylinder 1224.

Thus, the bed 10 is moved in the directions of the major axis and orthogonal axis of the bed 10, in accordance with the movement operation of the first slider 1222 in the major-axis direction and the extension/retraction operation of the hydraulic cylinder 1224 in the orthogonal-axis direction. With the movement of the bed 10, the top-plate 11 is moved in the directions of the major axis and orthogonal axis.

The top-plate moving mechanism 124 includes a second slider 1241, a second rail 1242, and a third rail 1243. The second rail 1242 and third rail 1243 are provided on the bottom surface of the top-plate 11. The second rail 1242 is disposed in the major-axis direction, and both ends thereof are movably supported by first side-surface grooves 1244 of the top-plate 11. The third rail 1243 is disposed in the minor-axis direction, and both ends thereof are movably supported by second side-surface grooves 1245 of the top-plate 11. The second slider 1241 includes a bearing which includes a plurality of rolling elements. The second slider 1241 is fixed on the top surface of the upper bed portion 101, and moves the second rail 1242 and third rail 123. The top-plate driver 123 drives the second slider 1241 in accordance with a control signal from the controller 19. By the driving of the second slider 1241, the rolling elements in the bearing are rolled along the second and third rails. By the movement of the second slider 1241, the top-plate 11 is moved in the minor-axis direction and major-axis direction. Incidentally, if the above-described movement of the bed 10 and top-plate 11 can be realized, the configuration of the moving unit 12 is not limited to the above example.

Thus, in the first embodiment, by the movement of the bed 10 and top-plate 11, the top-plate 11 is moved along the three orthogonal axes. However, by moving the top-plate 11, CT gantry 13 and PET gantry 14, the top-plate 11 may be relatively moved along the three orthogonal axes. A second embodiment, in which the top-plate 11 is moved along the three orthogonal axes, will be described later.

Next, a description is given of a phantom which is used for, e.g. calibration of the gamma ray detector in the medical imaging diagnosis apparatus 1 according to the first embodiment. FIG. 5 is a perspective view illustrating an example of a phantom used in, for example, calibration of the gamma ray detector in the medical imaging diagnosis apparatus 1 according to the first embodiment. FIG. 5 illustrates a cylindrical phantom T and a human body phantom H as examples of the phantom.

The cylindrical phantom T is used, for example, for evaluation of sensitivity characteristics of the gamma ray detector in the PET gantry 14. A radioactive isotope is disposed in the cylindrical phantom T.

The human body phantom H is used for comprehensive evaluation of quantitativity, including the effect of scattering/absorption by a substance, correction precision of scattering/absorption correction, and characteristics of image reconstruction. The human body phantom H has the shape of a thoracoabdominal region of the human body. A radioactive isotope with a known concentration is disposed in the human body phantom H. The radioactive isotope repeatedly emits positrons. The emitted positron combines with an electron near an emission point of the positron. If the positron combines with the electron, the positron and electron annihilate, and a pair of gamma rays are emitted in an approximately 180-degree direction. The gamma ray detector detects gamma rays emitted from the phantom. The gamma ray detector generates an electric signal, based on the energy of the detected gamma rays.

(First Top-Plate Position Adjustment Function)

A first top-plate position adjustment function is a function according to the first embodiment, wherein, by utilizing a CT image relating to a phantom placed on the top-plate 11, the position of the top-plate 11 is automatically adjusted in order to make the position of the characteristic point of the phantom agree with the PET center position. An operation according to the first top-plate position adjustment function (hereinafter "first top-plate position adjustment operation") is described with reference to FIG. 6.

Figure 6:
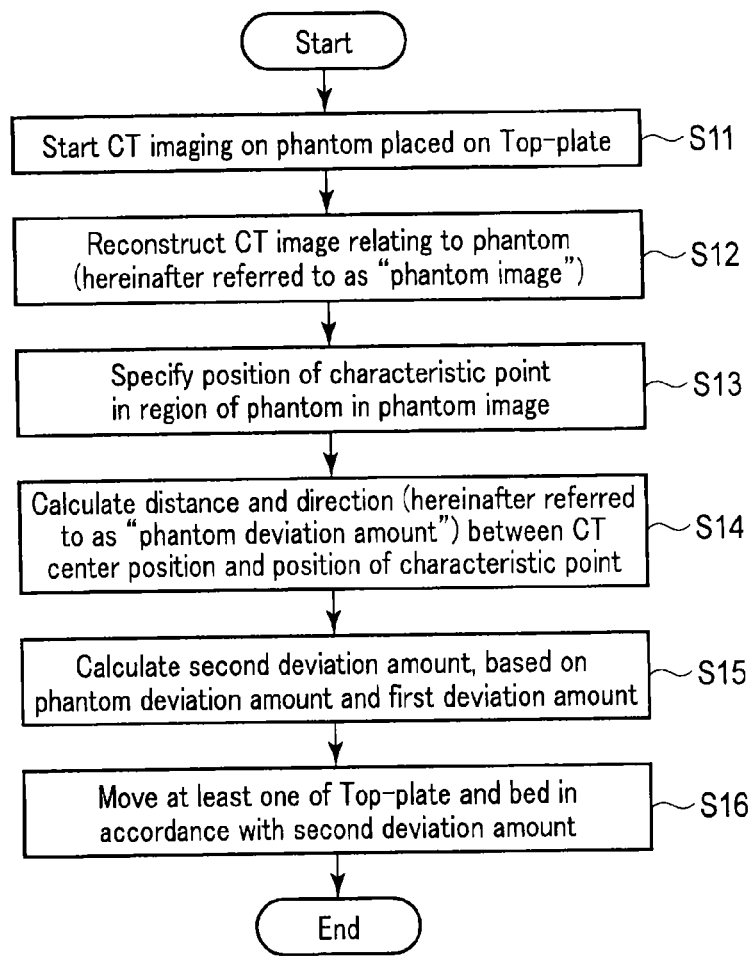
FIG. 6 relates to the first embodiment, and is a flowchart illustrating an example of the procedure of a first top-plate position adjustment operation.

FIG. 6 is a flowchart illustrating an example of the procedure of the first top-plate position adjustment operation by the medical imaging diagnosis apparatus 1 according to the first embodiment. Incidentally, in the description of FIG. 6, it is assumed that the first deviation amount, which is used for the calculation of the second deviation amount, is prestored in the storage unit 17.

In addition, for the purpose of simple description, it is assumed that the phantom, which is placed on the top-plate 11, has a cross-sectional shape which is uniform in the major-axis direction. Specifically, in FIG. 6, a description is given of top-plate position adjustment on two-dimensional coordinates constituted by the orthogonal axis and minor axis. However, the first top-plate position adjustment function is also applicable to top-plate position adjustment on three-dimensional coordinates constituted by adding the major axis to the orthogonal axis and minor axis.

The operator sets the phantom on the top-plate 11. Then, CT imaging relating to the phantom is started in accordance with an instruction by the operator through the input unit 18 (step S11). After the CT imaging, CT projection data relating to the phantom is generated by the CT projection data generator 15. Based on the CT projection data, the CT image relating to the phantom (hereinafter referred to as "phantom image") is reconstructed by the reconstruction unit 16 (step S12). In the phantom image, the position of the characteristic point of the phantom region is specified by the position specifying unit 20 (step S13). A distance and a direction (hereinafter referred to as "phantom deviation amount") of the position of the characteristic point to the CT center position is calculated by the calculator 21 (step S14).

The first deviation amount, which is stored in the storage unit 17, is read out by the controller 19. Based the phantom deviation amount and the first deviation amount, the second deviation amount is calculated by the calculator 21 (step S15). The calculated second deviation amount is stored in the storage unit 17. Based on the second deviation amount, the moving unit 12 is controlled by the controller 19. At least one of the top-plate 11 and the bed 10 is moved by the moving unit 12 (step S16). Thus, the position of the characteristic point of the phantom agrees with the PET center position.

Incidentally, the movement of the top-plate 11 and bed 10 may be executed in accordance with an input of the operator through the input unit 18. At this time, the display unit 22 displays the second deviation amount, and a difference (hereinafter referred to as "difference amount") between a movement amount of the top-plate moving mechanism 124 and bed moving mechanism 122 and the second deviation amount. The operator refers to the displayed second deviation amount and difference amount, and inputs, through the input unit 18, a movement amount of the top-plate moving mechanism 124 and bed moving mechanism 122. Based on the input movement amount, the controller 19 controls the moving unit 12. Then, at least one of the top-plate 11 and bed 10 is moved by the moving unit 12.

Figure 7:
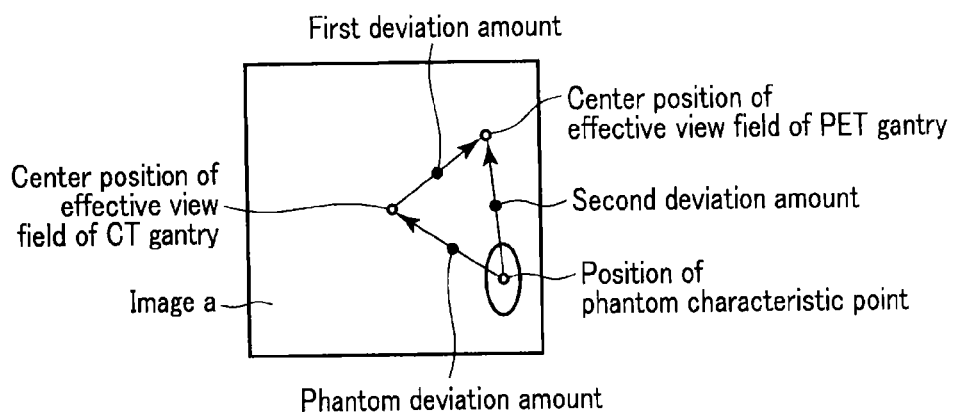
FIG. 7 is an explanatory view for explaining a first deviation amount stored in a storage unit of the medical imaging diagnosis apparatus according to the first embodiment, and a second deviation amount calculated by a calculator.

Next, a description is given of the first deviation amount stored in the storage unit 17 of the medical imaging diagnosis apparatus 1 according to the first embodiment, and the second deviation amount calculated by the calculator 21. FIG. 7 is an explanatory view for explaining the first deviation amount stored in the storage unit 17 of the medical imaging diagnosis apparatus 1 according to the first embodiment, and the second deviation amount calculated by the calculator 21. An image a in FIG. 7 is a CT image relating to the phantom.

The first deviation amount is expressed by a distance and a direction between the CT center position and the PET center position. Specifically, the first deviation amount is a vector (hereinafter referred to as "first vector amount"). The phantom deviation amount is expressed by a distance and a direction between the coordinates of the CT center position and the position coordinates of the characteristic point in the region of the phantom. Specifically, the phantom deviation amount is a vector (hereinafter referred to as "phantom deviation vector amount"). The second deviation amount calculated by the calculator 21 is expressed by a distance and a direction between the position of the characteristic point in the region of the phantom and the PET center position. Specifically, the second deviation amount is a vector (hereinafter referred to as "second vector amount") in which the first vector amount and the phantom deviation vector amount are compounded.

The calculator outputs the calculated second vector amount to the controller 19. The controller 19 controls the moving unit 12 in accordance with the second vector amount (second deviation amount).

Second Embodiment

Next, the details of a moving unit 12 of a medical imaging diagnosis apparatus 1 according to a second embodiment are described. FIG. 8 is a configuration diagram illustrating an example of the configuration of the moving unit 12 in the medical imaging diagnosis apparatus 1 according to the second embodiment. As illustrated in FIG. 8, the moving unit 12 includes a top-plate driver 123, a gantry driver 125, a top-plate moving mechanism 124, and a gantry moving mechanism 126.

The top-plate driver 123 drives the top-plate moving mechanism 124. The gantry driver 125 drives the gantry moving mechanism 126. Each of the top-plate driver 123 and the gantry driver 125 is, for example, a driving device such as a motor. The top-plate driver 123 and gantry driver 125 are driven in accordance with control signals from the controller 19. The top-plate moving mechanism 124 moves the top-plate 11 by the driving by the top-plate driver 123. The gantry moving mechanism 126 moves the CT gantry 13 and PET gantry 14 by the driving by the gantry driver 125. A detailed description of the top-plate moving mechanism 124 and gantry moving mechanism 126 will be given later.

Next, referring to FIG. 9, the configuration of the moving unit 12 according to the second embodiment is described. FIG. 9 relates to the moving unit 12 of the medical imaging diagnosis apparatus 1 according to the second embodiment, and is an external appearance view illustrating an example of the external appearance of the top-plate 11 and bed 10.

As illustrated in FIG. 9, the top-plate 11 is supported by a top-plate supporting mechanism 111. The top-plate moving mechanism 124 includes a fourth slider 1246, a fourth rail 1247, a fifth slider 1248, and a fifth rail 1249. The fourth slider 1246 is provided on the top-plate 11. The fourth rail 1247 and fifth slider 1248 are provided on the top-plate supporting mechanism 111. The fifth rail 1249 is provided on the bed 10. Each of the fourth and fifth sliders includes a bearing which includes a plurality of rolling elements. On the top-plate 11, the fourth rail 1247 is disposed along the minor-axis direction at a connection surface between the top-plate supporting mechanism 111 and top-plate 11. On the bed 10, the fifth rail 1249 is disposed in the orthogonal-axis direction at a connection surface between the top-plate supporting mechanism 111 and bed 10. A linear motion bearing is formed by the fourth slider 1246 and fourth rail 1247. A linear motion bearing is formed by the fifth slider 1248 and fifth rail 1249. The top-plate driver 123 drives the fourth and fifth sliders in accordance with control signals from the controller 19. By the driving of the fourth slider

1246, the rolling elements in the bearing are rolled along the fourth rail 1247. By the driving of the fifth slider 1248, the rolling elements in the bearing are rolled along the fifth rail 1249. By the movement of the fourth slider 1246, the top-plate 11 is moved in the minor-axis direction. By the movement of the fifth slider 1248, the top-plate 11 is moved in the orthogonal-axis direction.

The gantry moving mechanism 126 serves also as a connection housing for moving the CT gantry 13 together with the PET gantry 14. The gantry moving mechanism 126 includes a sixth slider 1261 and a sixth rail 1262. The sixth slider 1261 includes a bearing which includes a plurality of rolling elements. The sixth rail 1262 is disposed along the major-axis direction on an installation surface of the gantry moving mechanism 126. The sixth slider 1261 is fixed to the bottom surface of the housing of the gantry moving mechanism 126. The gantry driver 125 drives the sixth slider 1261 in accordance with a control signal from the controller 19. By the driving of the sixth slider 1261, the rolling elements in the bearing roll along the sixth rail 1262. By the movement of the sixth slider 1261, the CT gantry 13 and PET gantry 14 are moved in the major-axis direction. Incidentally, if the above-described movement of the top-plate 11, CT gantry 13 and PET gantry 14 can be realized, the configuration of the moving unit 12 is not limited to the above example.

Thus, in the second embodiment, by the movement of the top-plate 11, CT gantry 13 and PET gantry 14, the top-plate 11 is relatively moved along the three orthogonal axes.

(Second Top-Plate Position Adjustment Function)

A second top-plate position adjustment function is a function according to the second embodiment, wherein, by utilizing a CT image relating to a phantom placed on the top-plate 11, the position of the top-plate 11 is automatically adjusted in order to make the position of the characteristic point of the phantom agree with the PET center position. An operation according to the second top-plate position adjustment function (hereinafter "second top-plate position adjustment operation") is described with reference to FIG. 10.

In addition, for the purpose of simple description, it is assumed that the phantom, which is placed on the top-plate 11, has a cross-sectional shape which is uniform in the major-axis direction. Specifically, in FIG. 10, a description is given of top-plate position adjustment on two-dimensional coordinates constituted by the orthogonal axis and minor axis. However, the second top-plate position adjustment function is also applicable to top-plate position adjustment on three-dimensional coordinates constituted by adding the major axis to the orthogonal axis and minor axis.

Figure 10:
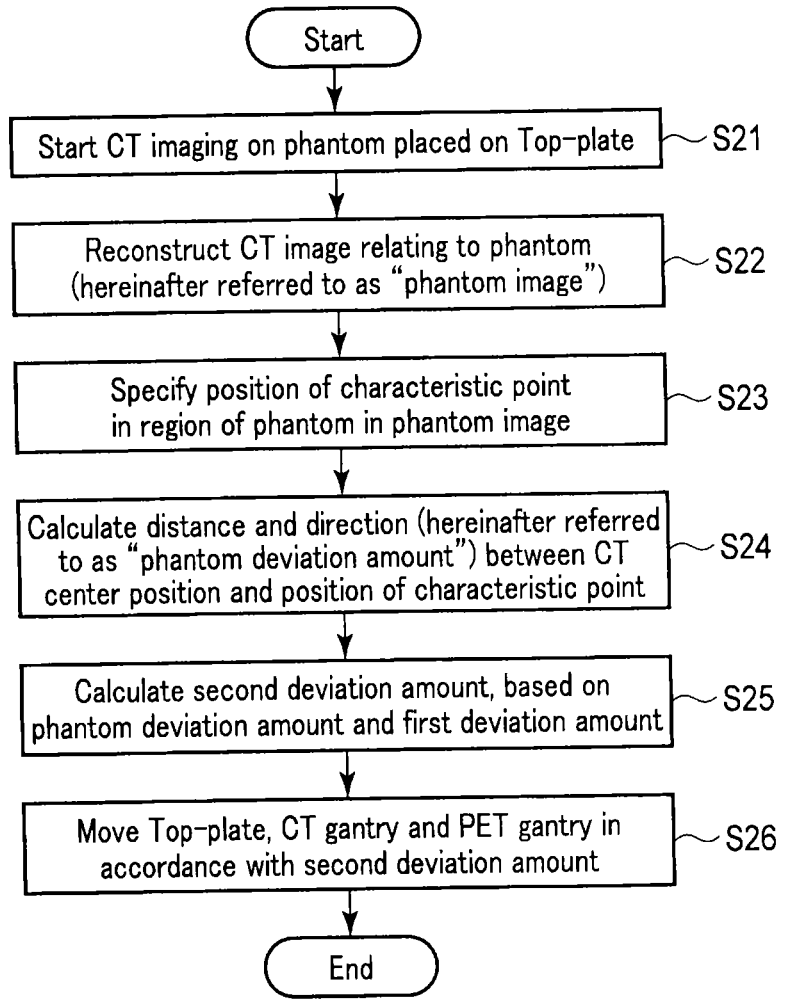
FIG. 10 relates to the second embodiment, and is a flowchart illustrating an example of the procedure of a second top-plate position adjustment operation.

FIG. 10 is a flowchart illustrating an example of the procedure of the second top-plate position adjustment operation by the medical imaging diagnosis apparatus 1 according to the second embodiment. Incidentally, in the description of FIG. 10, it is assumed that the first deviation amount, which is used for the calculation of the second deviation amount, is prestored in the storage unit 17.

The operator sets the phantom on the top-plate 11. Then, CT imaging relating to the phantom is started in accordance with an instruction by the operator through the input unit 18 (step S21). After the CT imaging, CT projection data relating to the phantom is generated by the CT projection data generator 15. Based on the CT projection data, the CT image relating to the phantom (hereinafter referred to as "phantom image") is reconstructed by the reconstruction unit 16 (step S22). In the phantom image, the position of the characteristic point of the phantom region is specified by the position specifying unit 20 (step S23). A distance and a direction (hereinafter referred to as "phantom deviation amount") of the position of the characteristic point to the CT center position is calculated by the calculator 21 (step S24).

The first deviation amount, which is stored in the storage unit 17, is read out by the controller 19. Based the phantom deviation amount and the first deviation amount, the second deviation amount is calculated by the calculator 21 (step S25). The calculated second deviation amount is stored in the storage unit 17. Based on the second deviation amount, the moving unit 12 is controlled by the controller 19. The top-plate 11, CT gantry 13 and PET gantry 14 are moved by the moving unit 12 (step S26). Thus, the position of the characteristic point of the phantom agrees with the PET center position.

Incidentally, the movement of the top-plate 11, CT gantry and PET gantry 14 may be executed in accordance with an input of the operator through the input unit 18. At this time, the display unit 22 displays the second deviation amount, and a difference (hereinafter referred to as "difference amount") between a movement amount of the top-plate moving mechanism 124 and gantry moving mechanism 126 and the second deviation amount. The operator refers to the displayed second deviation amount and difference amount, and inputs, through the input unit 18, a movement amount of the top-plate moving mechanism 124 and gantry moving mechanism 126. Based on the input movement amount, the controller 19 controls the moving unit 12. Then, the top-plate 11, CT gantry 13 and PET gantry 14 are moved by the moving unit 12.

According to the medical imaging diagnosis apparatuses 1 of the above-described first and second embodiments, the following advantageous effects can be obtained.

According to the medical imaging diagnosis apparatus 1 of the first embodiment, the characteristic point of the phantom can be specified from the CT image relating to the phantom placed on the top-plate 11. In addition, the distance and direction (phantom deviation amount) between the CT center position and the phantom characteristic point can be calculated. The distance and direction (first deviation amount) between the CT center position and PET center position is prestored in the storage unit 17. Based on these, the distance and direction (second deviation amount) between the center position of the effective view field in the PET gantry 14 and the characteristic point of the phantom can be calculated. In accordance with the second deviation amount, the controller 19 automatically controls the moving unit 12. The moving unit 12 moves at least one of the top-plate 11 and the bed 10. Specifically, by executing the CT imaging relating to the phantom placed on the top-plate 11, the top-plate 11 can automatically be moved in the orthogonal-axis (height) direction and in the major-axis and minor-axis directions (left-and-right movement) such that the center position of the effective view field in the PET gantry 14 agrees with the characteristic point of the phantom. In addition, by referring to the second deviation amount displayed on the display unit 22, the operator can manually move, through the input unit 18, at least one of the top-plate 11 and the bed 10.

From the above, according to the medical imaging diagnosis apparatus 1 of the first embodiment, it is possible to provide the medical imaging diagnosis apparatus 1 which can move a predetermined position of the phantom placed on the top-plate 11 to the center position of the effective view field of the nuclear medicine diagnosis apparatus. Thereby, when calibration is executed for the gamma ray detector of the PET detector, etc., the position adjustment of the phantom can be executed by CT scan. In addition, compared to the execution of position adjustment of the phantom by the operator's manual work, the center position of the phantom can more exactly be moved to the center position of the effective view field of the gamma ray detector. Hence, according to the medical imaging diagnosis apparatus 1 of the first embodiment, exact calibration can be executed. Specifically, at the time of calibrating the gamma ray detector (PET detector), the movement of the phantom can easily and exactly be executed.

According to the medical imaging diagnosis apparatus 1 of the second embodiment, the characteristic point of the phantom can be specified from the CT image relating to the phantom placed on the top-plate 11. In addition, the distance and direction (phantom deviation amount) between the CT center position and the phantom characteristic point can be calculated. The distance and direction (first deviation amount) between the CT center position and PET center position is prestored in the storage unit 17. Based on these, the distance and direction (second deviation amount) between the center position of the effective view field in the PET gantry 14 and the characteristic point of the phantom can be calculated. In accordance with the second deviation amount, the controller 19 automatically controls the moving unit 12. The moving unit 12 moves the top-plate 11, CT gantry 13 and PET gantry 14. Specifically, by executing the CT imaging relating to the phantom placed on the top-plate 11, the top-plate 11 can automatically be moved in the orthogonal-axis (height) direction and in the major-axis and minor-axis directions (left-and-right movement) such that the center position of the effective view field in the PET gantry 14 agrees with the characteristic point of the phantom. In addition, by referring to the second deviation amount displayed on the display unit 22, the operator can manually move, through the input unit 18, the top-plate 11, CT gantry 13 and PET gantry 14.

From the above, according to the medical imaging diagnosis apparatus 1 of the second embodiment, it is possible to provide the medical imaging diagnosis apparatus 1 which can move a predetermined position of the phantom placed on the top-plate 11 to the center position of the effective view field of the nuclear medicine diagnosis apparatus. Thereby, when calibration is executed for the gamma ray detector of the PET detector, etc., the position adjustment of the phantom can be executed by CT scan. In addition, compared to the execution of position adjustment of the phantom by the operator's manual work, the center position of the phantom can more exactly be moved to the center position of the effective view field of the nuclear medicine diagnosis apparatus. Hence, according to the medical imaging diagnosis apparatus 1 of the second embodiment, exact calibration can be executed. Specifically, at the time of calibrating the gamma ray detector (PET detector), the movement of the phantom can easily and exactly be executed.

Third Embodiment

Next, a medical imaging diagnosis apparatus 1 according to a third embodiment is described. In the first embodiment and second embodiment, the description was given of the adjusting method of the position of the top-plate 11 in the calibration work of the nuclear medicine diagnosis apparatus with use of the phantom. The first embodiment and second embodiment are also applicable when a subject is imaged. In the third embodiment, a description is given of top-plate position adjustment at a time of imaging a subject. The configuration of the medical imaging diagnosis apparatus 1 according to the third embodiment is the same as in the first embodiment. Hereinafter, differences from the first embodiment and second embodiment will be described.

FIG. 11 is a flowchart illustrating an example of an imaging procedure of a subject with use of the medical imaging diagnosis apparatus 1 according to the third embodiment.

(Step S31) Adjustment of the Position of Top-Plate 11

The position of a subject placed on the top-plate 11 is adjusted by the operator. Specifically, the operator places the subject on the top-plate 11, for example, such that the body axis of the subject agrees with the major axis of the top-plate 11. Then, the operator moves, through the input unit 18, the top-plate 11 such that the center position of the subject agrees with the CT center position, by using a projector as a guide. Specifically, in step S31, the subject is moved to a position for CT imaging.

(Step S32) Execution of CT Imaging on the Subject

CT imaging on the subject is started in accordance with an instruction by the operator through the input unit 18. Then, in accordance with control by the controller 19, the top-plate 11 is moved by the moving unit 12 into the hollow portion 131 of the CT gantry 13. Subsequently, CT imaging is executed. At this time, based on an output from the X-ray detector, CT projection data relating to the subject is generated by the projection data generator 15. Then, based on the CT projection data, a CT image relating to the subject is generated by the reconstruction unit 16.

(Step S33) Movement of the Top-Plate 11 to the Position for PET Imaging

If the CT imaging is completed, the top-plate 11 is moved by the moving unit 12 from the hollow portion 131 of the CT gantry 13 back to the position prior to the CT imaging, in accordance with control by the controller 19. Then, in accordance with control by the controller 19, the top-plate 11 is moved by the moving unit 12, relative to the PET center position. Specifically, in step S33, the top-plate 11 and the subject placed on the top-plate 11 are moved from the position for CT imaging to the position for PET imaging.

(Step S34) Execution of PET Imaging on the Subject

A radioactive tracer is administered to the subject. Then, in accordance with control by the controller 19, the top-plate 11 is moved by the moving unit 12 into the hollow portion 141 of the PET gantry 14, and PET imaging is executed.

Next, the details of the procedure of step S33 are described with reference to FIG. 12 and FIG. 13.

FIG. 12 is a flowchart illustrating an example of the procedure of step S33.

FIG. 13 is an explanatory view for explaining a third deviation amount which is calculated by the calculator 21.

(Step S41) Specifying of the Position of the Characteristic Point of the Subject The position specifying unit 20 specifies, in a predetermined coordinate system, a predetermined position (hereinafter referred to as "characteristic point of subject") of the subject on the reconstructed CT image of the subject. The characteristic point is a point desired by the operator, and is, for example, the center position, the position of the center of gravity, etc. of the subject.

(Step S42) Specifying of a Subject Deviation Amount

The calculator 21 calculates a distance and a direction (comprehensively referred to as "subject deviation amount") of the position of the characteristic point of subject relative to the CT center position.

(Step S43) Calculation of a Third Deviation Amount

Based on the first deviation amount and the subject deviation amount, the calculator 21 calculates a third deviation amount. The third deviation amount designates a deviation amount between the position of the characteristic point of subject and the PET center position.

(Step S44) Movement of the Subject to the Position for PET Imaging.

In accordance with the third deviation amount, the top-plate 11 is relatively moved by the moving unit 12. For example, the top-plate 11 is moved by the moving unit 12. Incidentally, the PET gantry 14 may be moved by the moving unit 12, or the top-plate 11 and PET gantry 14 may be moved by the moving unit 12. Thereby, the subject is moved to the position for PET imaging.

According to the medical imaging diagnosis apparatus 1 of the above-described third embodiment, the first deviation (the deviation amount between the center positions of the apparatuses) can be specified based on the PET center position and CT center position. In addition, the subject deviation amount between the center position of the subject at the time of CE imaging and the CT center position can be specified based on the reconstruction image of the subject. Then, based on the first deviation amount and the subject deviation amount, the third deviation amount, which is indicative of the deviation amount between the center position of the subject and the PET center position, can be specified. In accordance with the third deviation amount, the moving unit 12 moves the top-plate 11, and thereby the center position of the subject can be made to agree with the PET center position. Thus, PET imaging can be executed with high precision.

In the meantime, in the third embodiment, the description has been given of the adjustment method of the position of the top-plate 11 for making the center position of the subject agree with the PET center position. However, in order to align the PET center position with the CT center position, the position of the top-plate 11 may automatically be adjusted. Specifically, in accordance with the above-described first deviation amount, the top-plate 11 may be relatively moved by the moving unit 12. Thereby, the positional relationship of the center position of the subject to the CT center position agrees with the positional relationship of the center position of the subject to the PET center position. Accordingly, although there is a possibility that the center position of the subject does not agree with the PET center position, the center position of the subject at the time of CT imaging and the center position of the subject at the time of PET imaging can be set on the same axis. Thus, the center position of the reconstructed CT image agrees with the center position of the reconstructed PET image, and a process for positional adjustment in the fusion image is made needless.

In addition, in the first, second and third embodiments, the description was given of the medical imaging diagnosis apparatus 1 which includes the CT gantry 13 and PET gantry 14. However, the embodiments are not limited to the medical imaging diagnosis apparatus 1 which includes the CT gantry 13 and PET gantry 14.

Fourth Embodiment

FIG. 14 is a configuration diagram illustrating an example of the configuration of an X-ray CT apparatus 2 according to a fourth embodiment. Differences from the first, second and third embodiments will mainly be described.

As illustrated in FIG. 14, the X-ray CT apparatus 2 is connected to a nuclear medicine diagnosis apparatus 3 over a network such as a LAN (Local Area Network) or a public electronic communication network. The nuclear medicine diagnosis apparatus 3 is, for instance, a PET apparatus or a SPECT apparatus. For example, the nuclear medicine diagnosis apparatus 3 includes a second gantry 14. The second gantry is, for example, a PET gantry. A top-plate 11, which the X-ray CT apparatus 2 includes, is also used for imaging by the PET gantry 14 of the nuclear medicine diagnosis apparatus 3. Therefore, CT imaging by the X-ray CT apparatus 2 and PET imaging by the nuclear medicine diagnosis apparatus 3 can be executed on the subject placed on the top-plate 11.

The X-ray CT apparatus 2 includes a transmission/reception unit 23b for connection to an external device over the network. The transmission/reception unit 23b includes, for example, a connector unit (not shown) for connection to an external device, etc. by a wire cable, etc., and a wireless signal receiver (not shown) for receiving a wireless signal from the external device. In accordance with control of the controller 19, the X-ray CT apparatus 2 transmits/receives data to/from the nuclear medicine diagnosis apparatus 3. For example, in accordance with control of the controller 19, the X-ray CT apparatus 2 receives, from the nuclear medicine diagnosis apparatus 3, data relating to a center position (PET center position) of the effective view field in the second gantry 14. The received data relating to the PET center position is stored in the storage unit 17.

The storage unit 17 stores data of the CT center position of a first gantry 13 (CT gantry 13).

The calculator 21 calculates the first deviation amount, based on the data of the PET center position, which was received from the nuclear medicine diagnosis apparatus 3, and the data of the CT center position stored in the storage unit 17. The data of the first deviation amount, which was calculated by the calculator 21, is stored in the storage unit 17. In addition, based on the reconstruction image relating to the subject, which was generated by the reconstruction unit 16, the calculator 21 calculates the subject deviation amount between the center position of the subject at the time of CT imaging and the CT center position. Then, based on the first deviation amount and subject deviation amount, the calculator 21 calculates the third deviation amount which is indicative of the deviation amount between the center position of the subject and the PET center position.

In accordance with the first deviation amount, the moving unit 12 moves the top-plate 11 relative to the PET center position. Incidentally, in accordance with the third deviation amount, the moving unit 12 may move the top-plate 11 relative to the PET center position.

Incidentally, a control device 5, which is composed of the storage unit 17, input unit 18, controller 19, position specifying unit 20, calculator 21, display unit 22 and transmission/reception unit 23b that are included in the X-ray CT apparatus 2 according to the fourth embodiment, may be configured as an independent device. At this time, the control device 5 receives, from the nuclear medicine diagnosis apparatus 3, data relating to the center position (PET center position) of the effective view field in the second gantry 14. In addition, the control device 5 receives, from the CT apparatus 2, data relating to the center position (CT center position) of the effective view field of the first gantry 13. Then, the control device 5 calculates the first deviation amount, based on the PET center position and the CT center position, and transmits the data of the first deviation amount to the CT apparatus 2. In accordance with the received data of the first deviation amount, the CT apparatus 2 moves the top-plate 11 relative to the PET center position. Incidentally, the control device 5 may receive, from the CT apparatus 2, the data of the reconstruction image relating to the subject, or the data relating to the position of the characteristic point of the subject. At this time, the control device 5 transmits the data of the third deviation amount to the CT apparatus 2. In accordance with the received data of the third deviation amount, the CT apparatus 2 moves the top-plate 11 relative to the PET center position.

According to the above-described fourth embodiment, the same advantageous effects as with the medical imaging diagnosis apparatuses 1 according to the first, second and third embodiments can be obtained. Specifically, the X-ray CT apparatus 2 can move, based on the first deviation amount, the position of the subject, which has been in alignment with the CT center position, to the PET center position of the PET gantry 14. Accordingly, although there is a possibility that the center position of the subject does not agree with the PET center position, the center position of the subject at the time of CT imaging and the center position of the subject at the time of PET imaging can be set on the same axis. Thus, the center position of the reconstructed CT image agrees with the center position of the reconstructed PET image, and a process for positional adjustment in the fusion image is made needless.

Furthermore, based on the third deviation amount, the X-ray CT apparatus 2 can move the center position of the subject to the PET center position of the PET gantry 14. Since the center position of the subject can be made to agree with the PET center position, PET imaging can be executed with high precision.

Fifth Embodiment

FIG. 15 is a configuration diagram illustrating an example of the configuration of a nuclear medicine diagnosis apparatus 3 according to a fifth embodiment. Differences from the first, second and third embodiments will mainly be described.

As illustrated in FIG. 15, the nuclear medicine diagnosis apparatus 3 is connected to an X-ray CT apparatus 2 over a network such as a LAN (Local Area Network) or a public electronic communication network. The nuclear medicine diagnosis apparatus 3 is, for instance, a PET apparatus or a SPECT apparatus. For example, the nuclear medicine diagnosis apparatus 3 includes a second gantry 14. The second gantry is, for example, a PET gantry. A top-plate 11, which the nuclear medicine diagnosis apparatus 3 includes, is also used for imaging by a first gantry 13 (CT gantry 13) of the X-ray CT apparatus 2. Therefore, PET imaging by the nuclear medicine diagnosis apparatus 3 and CT imaging by the X-ray CT apparatus 2 can be executed on the subject placed on the top-plate 11.

The nuclear medicine diagnosis apparatus 3 includes a transmission/reception unit 23a for connection to an external device over the network. The transmission/reception unit 23a includes, for example, a connector unit (not shown) for connection to an external device, etc. by a wire cable, etc., and a wireless signal receiver (not shown) for receiving a wireless signal from the external device. In accordance with control of the controller 19, the nuclear medicine diagnosis apparatus 3 transmits/receives data to/from the X-ray CT apparatus 2. For example, in accordance with control of the controller 19, the nuclear medicine diagnosis apparatus 3 receives, from the X-ray CT apparatus 2, data relating to a center position (CT center position) of the effective view field in the first gantry 13. The received data relating to the CT center position is stored in the storage unit 17. Furthermore, in accordance with control of the controller 19, the nuclear medicine diagnosis apparatus 3 receives, from the X-ray CT apparatus 2, data of a reconstruction image relating the subject, or data relating to the position of the characteristic point of the subject.

The storage unit 17 stores data of the PET center position of the second gantry 14.

The calculator 21 calculates the first deviation amount, based on the data of the CT center position, which was received from the X-ray CT apparatus 2, and the data of the PET center position stored in the storage unit 17. The data of the first deviation amount, which was calculated by the calculator 21, is stored in the storage unit 17. In addition, based on the position of the characteristic point of the subject or the reconstruction image relating to the subject, which was received from the X-ray CT apparatus 2, the calculator 21 calculates the subject deviation amount between the center position of the subject at the time of CT imaging and the CT center position. Then, based on the first deviation amount and subject deviation amount, the calculator 21 calculates the third deviation amount which is indicative of the deviation amount between the center position of the subject and the PET center position. The position of the characteristic point of the subject may be specified by the position specifying unit 20 from the reconstruction image relating to the subject, which was received from the X-ray CT apparatus 2.

In accordance with the first deviation amount, the moving unit 12 moves the top-plate 11 relative to the PET center position. Incidentally, in accordance with the third deviation amount, the moving unit 12 may move the top-plate 11 relative to the PET center position.

Incidentally, a control device 5, which is composed of the storage unit 17, input unit 18, controller 19, position specifying unit 20, calculator 21, display unit 22 and transmission/reception unit 23a that are included in the nuclear medicine diagnosis apparatus 3 according to the fifth embodiment, may be configured as an independent device. At this time, the control device 5 receives, from the nuclear medicine diagnosis apparatus 3, data relating to the center position (PET center position) of the effective view field in the second gantry 14. In addition, the control device 5 receives, from the X-ray CT apparatus 2, data relating to the center position (CT center position) of the effective view field of the first gantry 13. Then, the control device 5 calculates the first deviation amount, based on the PET center position and the CT center position, and transmits the data of the first deviation amount to the X-ray CT apparatus 2. In accordance with the received data of the first deviation amount, the X-ray CT apparatus 2 moves the top-plate 11 relative to the PET center position. Incidentally, the control device 5 may receive, from the X-ray CT apparatus 2, the data of the reconstruction image relating to the subject, or the data relating to the position of the characteristic point of the subject. At this time, the control device 5 transmits the data of the third deviation amount to the nuclear medicine diagnosis apparatus 3. In accordance with the received data of the third deviation amount, the nuclear medicine diagnosis apparatus 3 moves the top-plate 11 relative to the PET center position.

According to the above-described fifth embodiment, the same advantageous effects as with the medical imaging diagnosis apparatuses 1 according to the first, second and third embodiments can be obtained. Specifically, the nuclear medicine diagnosis apparatus 3 can move, based on the first deviation amount, the position of the subject, which has been in alignment with the CT center position, to the PET center position of the PET gantry 14. Accordingly, although there is a possibility that the center position of the subject does not agree with the PET center position, the center position of the subject at the time of CT imaging and the center position of the subject at the time of PET imaging can be set on the same axis. Thus, the center position of the reconstructed CT image agrees with the center position of the reconstructed PET image, and a process for positional adjustment in the fusion image is made needless.

Furthermore, based on the third deviation amount, the nuclear medicine diagnosis apparatus 3 can move the center position of the subject to the PET center position of the PET gantry 14. Since the center position of the subject can be made to agree with the PET center position, PET imaging can be executed with high precision.

Sixth Embodiment

Figure 16:
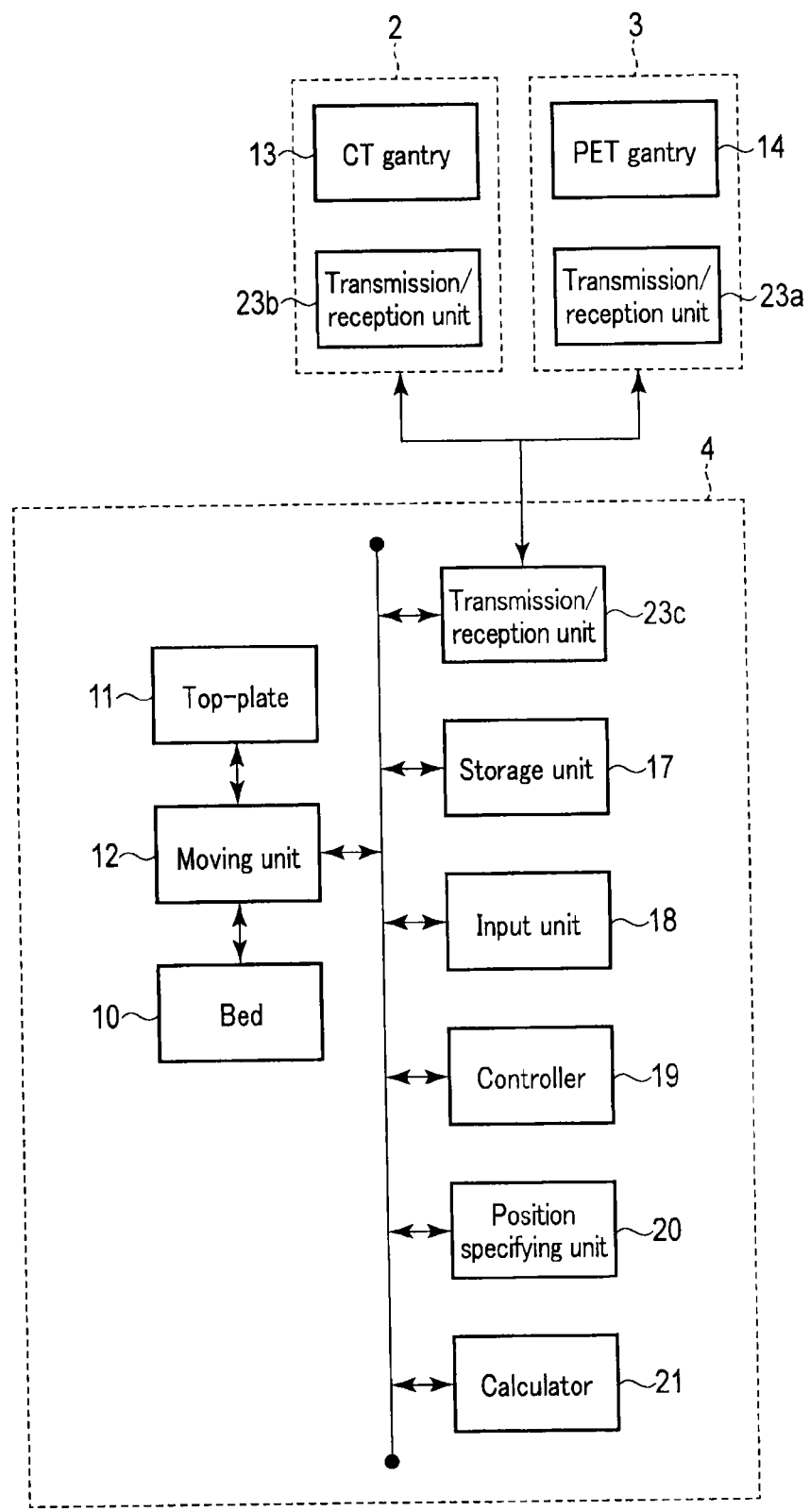
FIG. 16 is a configuration diagram illustrating an example of the configuration of a bed apparatus according to a sixth embodiment.

FIG. 16 is a configuration diagram illustrating an example of the configuration of a bed apparatus 4 according to a sixth embodiment. Differences from the first, second and third embodiments will mainly be described.

As illustrated in FIG. 16, the bed apparatus 4 is connected to an X-ray CT apparatus 2 and a nuclear medicine diagnosis apparatus 3 over a network such as a LAN (Local Area Network) or a public electronic communication network. The nuclear medicine diagnosis apparatus 3 is, for instance, a PET apparatus or a SPECT apparatus. The X-ray CT apparatus 2 includes a CT gantry 13 for imaging a subject by X-rays. The nuclear medicine diagnosis apparatus 3 includes a PET gantry 14 for detecting gamma rays emitted from the subject. A top-plate 11, which the bed apparatus 4 includes, is used for imaging by a first gantry 13 (CT gantry 13) of the X-ray CT apparatus 2 and for imaging by a second gantry 14 (PET gantry 14) of the nuclear medicine diagnosis apparatus 3. Therefore, PET imaging by the nuclear medicine diagnosis apparatus 3 and CT imaging by the X-ray CT apparatus 2 can be executed on the subject placed on the top-plate 11.

The bed apparatus 4 includes a transmission/reception unit 23c for connection to an external device over the network. The transmission/reception unit 23c includes, for example, a connector unit (not shown) for connection to an external device, etc. by a wire cable, etc., and a wireless signal receiver (not shown) for receiving a wireless signal from the external device. In accordance with control of the controller 19, the bed apparatus 4 transmits/receives data to/from the X-ray CT apparatus 2 and nuclear medicine diagnosis apparatus 3. For example, in accordance with control of the controller 19, the bed apparatus 4 receives, from the X-ray CT apparatus 2, data relating to a center position (CT center position) of the effective view field in the first gantry 13. Incidentally, in accordance with control of the controller 19, the bed apparatus 4 may receive, from the X-ray CT apparatus 2, data of a reconstruction image relating the subject, or data relating to the position of the characteristic point of the subject. In addition, in accordance with control of the controller 19, the bed apparatus 4 receives, from the nuclear medicine diagnosis apparatus 3, data relating to a center position (PET center position) of the effective view field in the second gantry 14. These received data are stored in the storage unit 17.

The calculator 21 calculates the first deviation amount, based on the data of the CT center position, which was received from the X-ray CT apparatus 2, and the data of the PET center position, which was received from the nuclear medicine diagnosis apparatus 3. The data of the first deviation amount, which was calculated by the calculator 21, is stored in the storage unit 17. In addition, based on the position of the characteristic point of the subject or the reconstruction image relating to the subject, which was received from the X-ray CT apparatus 2, the calculator 21 calculates the subject deviation amount between the center position of the subject at the time of CT imaging and the CT center position. Then, based on the first deviation amount and subject deviation amount, the calculator 21 calculates the third deviation amount which is indicative of the deviation amount between the center position of the subject and the PET center position. The position of the characteristic point of the subject may be specified by the position specifying unit 20 from the reconstruction image relating to the subject, which was received from the X-ray CT apparatus 2.

In accordance with the first deviation amount, the moving unit 12 moves the top-plate 11 relative to the PET center position. Incidentally, in accordance with the third deviation amount, the moving unit 12 may move the top-plate 11 relative to the PET center position.

In the meantime, although the display unit 22 is not included in the configuration of the bed apparatus 4 illustrated in FIG. 16, the display unit 22 may be included. In addition, if the operator can input an instruction to the bed apparatus 4 through the input unit 18, a display of some other apparatus (X-ray CT apparatus 2 or nuclear medicine diagnosis apparatus 3) may be used.

According to the above-described sixth embodiment, the same advantageous effects as with the medical imaging diagnosis apparatuses 1 according to the first, second and third embodiments can be obtained. Specifically, the bed apparatus 4 can move, based on the first deviation amount, the position of the subject, which has been in alignment with the CT center position, to the PET center position of the PET gantry 14. Accordingly, although there is a possibility that the center position of the subject does not agree with the PET center position, the center position of the subject at the time of CT imaging and the center position of the subject at the time of PET imaging can be set on the same axis. Thus, the center position of the reconstructed CT image agrees with the center position of the reconstructed PET image, and a process for positional adjustment in the fusion image is made needless.

Furthermore, based on the third deviation amount, the bed apparatus 4 can move the center position of the subject to the PET center position of the PET gantry 14. Since the center position of the subject can be made to agree with the PET center position, PET imaging can be executed with high precision.

According to the embodiments, medical imaging diagnosis apparatus, an X-ray CT apparatus, a nuclear medicine diagnosis apparatus, and a bed apparatus, which can move a predetermined position of a phantom and a subject placed on a top-plate to the center position of an effective view field of the nuclear medicine diagnosis apparatus can be provided.

While certain embodiments have been described, these embodiments have been presented by way of example only, and are not intended to limit the scope of the inventions. Indeed, the embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical imaging diagnosis apparatus comprising:
a top-plate configured for a subject to be placed thereon;

a bed configured to support the top-plate;
a first gantry including an X-ray generator and an X-ray detector which revolve around the top-plate;
a second gantry including a gamma ray detector configured to detect gamma rays emitted from the subject;
a processing circuitry configured to reconstruct a reconstruction image including a characteristic point of the subject, based on output data from the X-ray detector; and
a moving assembly configured to move, based on a first position indicative of a center position of an effective view field in the first gantry, a second position indicative of a center position of an effective view field in the second gantry, and a third position indicative of a position of the characteristic point, the top-plate to a position where the third position relative to the first position agrees with the second position relative to the first position.

2. The medical imaging diagnosis apparatus of claim 1, wherein the moving assembly is configured to move the top-plate, after an end of imaging of the subject by the first gantry and before a start of imaging of the subject by the second gantry.

3. A medical imaging diagnosis apparatus comprising:
a top-plate configured for a phantom to be placed thereon;
a bed configured to support the top-plate;
a first gantry including an X-ray generator and an X-ray detector which revolve around the top-plate;
a second gantry including a gamma ray detector configured to detect gamma rays emitted from the phantom;
a storage configured to store a first deviation amount between a first position indicative of a center position of an effective view field in the first gantry and a second position indicative of a center position of an effective view field in the second gantry;
a processing circuitry configured to reconstruct a reconstruction image relating to the phantom, based on output data from the X-ray detector and to calculate, based on a second deviation amount between a third position indicative of a characteristic point of a region relating to the phantom in the reconstruction image and the first position, and on the first deviation amount, a distance and a direction from the third position to the second position; and
a moving assembly configured to move the top-plate to a position where the third position relative to the first position agrees with the second position relative to the first position, in accordance with the distance and the direction.

4. The medical imaging diagnosis apparatus of claim 3, wherein the moving assembly is configured to move at least one of the top-plate and the bed, in accordance with the distance and the direction.

5. The medical imaging diagnosis apparatus of claim 3, wherein the moving assembly is configured to move at least one of the top-plate and the second gantry, in accordance with the distance and the direction.

6. The medical imaging diagnosis apparatus of claim 3, wherein the characteristic point is a center position of the region.

7. The medical imaging diagnosis apparatus of claim 3, wherein the characteristic point is a position of a center of gravity of the region.

8. The medical imaging diagnosis apparatus of claim 3, further comprising:
a display configured to display the reconstruction image; and
an interface configured to input the characteristic point in accordance with an operation instruction by an operator on the displayed reconstruction image.

9. An X-ray CT apparatus capable of transmission/reception of data to/from a nuclear medicine diagnosis apparatus including a second gantry including a gamma ray detector configured to detect gamma rays emitted from a subject, the X-ray CT apparatus comprising:
a transmitter/receiver configured to receive, from the nuclear medicine diagnosis apparatus, data relating to a second position indicative of a center position of an effective view field in the second gantry;
a top-plate configured for the subject to be placed thereon;
a first gantry including an X-ray generator and an X-ray detector which revolve around the top-plate;
a processing circuitry configured to reconstruct a reconstruction image including a characteristic point of the subject, based on output data from the X-ray detector; and
a moving assembly configured to move, based on a first position indicative of a center position of an effective view field in the first gantry, the second position, and a third position indicative of a position of the characteristic point, the top-plate to a position where the third position relative to the first position agrees with the second position relative to the first position.

10. A nuclear medicine diagnosis apparatus capable of transmission/reception of data to/from an X-ray CT apparatus including a first gantry including an X-ray generator and an X-ray detector which revolve around a subject, and a processing circuitry configured to reconstruct a reconstruction image including a characteristic point of the subject, based on output data from the X-ray detector, the nuclear medicine diagnosis apparatus comprising:
a transmitter/receiver configured to receive, from the X-ray CT apparatus, data relating to a first position indicative of a center position of an effective view field in the first gantry, and data relating to a third position indicative of a position of the characteristic point;
a top-plate configured for the subject to be placed thereon;
a second gantry including a gamma ray detector configured to detect gamma rays emitted from the subject; and
a moving assembly configured to move, based on the first position, a second position indicative of a center position of an effective view field in the second gantry, and the third position, the top-plate to a position where the third position relative to the first position agrees with the second position relative to the first position.

11. A bed apparatus capable of transmission/reception of data to/from a nuclear medicine diagnosis apparatus and an X-ray CT apparatus, comprising:
a top-plate;
a receiver configured to receive, from the nuclear medicine diagnosis apparatus, data relating to a first position indicative of a center position of an effective view field in a gantry of the nuclear medicine diagnosis apparatus, and to receive, from the X-ray CT apparatus, data relating to a second position indicative of a center position of an effective view field in a gantry of the X-ray CT apparatus; and
a moving assembly configured to move the top-plate relative to the second position, based on the first position and the second position.

* * * * *